US012644889B2

(12) United States Patent
Young et al.

(10) Patent No.: US 12,644,889 B2
(45) Date of Patent: Jun. 2, 2026

(54) VIRAL CONDENSATES AND METHODS OF USE THEREOF

(71) Applicant: Whitehead Institute for Biomedical Research, Cambridge, MA (US)

(72) Inventors: Richard A. Young, Boston, MA (US); Isaac Klein, Milton, MA (US); Ann Boija, Somerville, MA (US); Ozgur Oksuz, Worcester, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 699 days.

(21) Appl. No.: 18/011,457

(22) PCT Filed: Jun. 21, 2021

(86) PCT No.: PCT/US2021/038314

§ 371 (c)(1),
(2) Date: Dec. 19, 2022

(87) PCT Pub. No.: WO2021/258075

PCT Pub. Date: Dec. 23, 2021

(65) Prior Publication Data

US 2023/0236190 A1    Jul. 27, 2023

Related U.S. Application Data

(60) Provisional application No. 63/041,105, filed on Jun. 18, 2020.

(51) Int. Cl.
*G01N 33/569* (2006.01)
*G01N 33/58* (2006.01)

(52) U.S. Cl.
CPC ..... *G01N 33/56983* (2013.01); *G01N 33/582* (2013.01); *G01N 2333/165* (2013.01); *G01N 2469/10* (2013.01)

(58) Field of Classification Search
None
See application file for complete search history.

(56) References Cited

U.S. PATENT DOCUMENTS 6,635,416 B2 * 10/2003 Palese ..................... A61P 31/00
                                                435/235.1
2021/0340189 A1 * 11/2021 Liang ............... G01N 33/56983

FOREIGN PATENT DOCUMENTS

WO    WO-2019183552 A2    9/2019

OTHER PUBLICATIONS

Fung et al. (Annual Reviews, Sep. 2019, p. 529-557).*
Jack et al. (bioRxiv, Mar. 29, 2021).*
Ditlev, et al., Who's in and Who's Out-Compositional Control of Biomolecular Condensates, *J. Mol. Biol.*; 430(23):4666-4684, Nov. 2, 2018.
Klein, et al., "Partitioning of cancer therapeutics in nuclear condensates," *Science*;368(6497):1386-1392, Jun. 19, 2020.
Wheeler, et al., "Controlling compartmentalization by non-membrane-bound organelles," *Philos. Trans. R. Soc. Lond. B. Biol. Sci.*; 373(1747), May 26, 2018.
Young, Richard, "Transcriptional regulatory networks in living cells," GM123511; Funding date: Jul. 1, 2017-Jul. 1, 2020.
International Search Report for International Application No. PCT/US2021/38314 mailed Jan. 13, 2022.

* cited by examiner

*Primary Examiner* — Agnieszka Boesen
(74) *Attorney, Agent, or Firm* — Morse, Barnes-Brown & Pendleton, P.C.; Lisa M. Warren, Esq.; Daniel L. Branson, Esq.

(57) ABSTRACT

Provided herein are methods of screening for agents that can partition in viral condensates and therefore may be effective anti-viral agents. Also disclosed are methods of optimizing the activity and reducing the side effects of known or suspected anti-viral agents by screening the portioning of modified known or suspected anti-viral agents in viral condensates and other condensates occurring in cells (e.g., transcriptional condensates).

20 Claims, 6 Drawing Sheets

Specification includes a Sequence Listing.

SEQUENCE LISTING

<160> NUMBER OF SEQ ID NOS: 1

<210> SEQ ID NO 1
<211> LENGTH: 14
<212> TYPE: PRT
<213> ORGANISM: Artificial
<220> FEATURE:
<223> OTHER INFORMATION: amino acid linker sequence

<400> SEQUENCE: 1

Gly Ala Pro Gly Ser Ala Gly Ser Ala Ala Gly Gly Ser Gly
1               5                   10

VIRAL CONDENSATES AND METHODS OF USE THEREOF

RELATED APPLICATIONS

This application is a national stage filing under 35 U.S.C. 371 of International Application No. PCT/US2021/038314, filed Jun. 21, 2021, which claims the benefit of U.S. Provisional Application No. 63/041,105, filed on Jun. 18, 2020. The entire teachings of the above application are incorporated herein by reference. International Application No. PCT/US2021/038314 was published under PCT Article 21(2) in English.

GOVERNMENT SUPPORT

This invention was made with government support under GM123511 awarded by The National Institutes of Health. The government has certain rights in the invention.

BACKGROUND OF THE INVENTION

Viral infections, including SARS-CoV-2 viral infections, are a serious public health crisis. However, few effective anti-viral agents are currently available, and there exists an urgent need for new anti-viral agents especially for the treatment of SARS-CoV-2 or possible future novel virus pandemics.

SUMMARY OF THE INVENTION

The inventors have surprisingly shown that SARS-CoV-2 proteins form in vitro condensates and that some agents preferentially partition into the condensates even in the absence of targets for the agent. For instance, as shown herein, the DNA intercalator mitoxantrone partitions into SARS-CoV-2 nucleocapsid condensates not containing DNA. Thus, disclosed herein are methods of screening for agents that partition into viral condensates. Furthermore, disclosed herein are assays for identifying modified anti-viral agents having higher partition coefficients in viral condensates. Such modified anti-viral agents would be expected to be more effective for treating viral infections.

Some aspects of the present disclosure are directed to a method of characterizing an agent, comprising contacting the agent with a composition comprising a condensate comprising a viral protein or fragment thereof, and measuring incorporation of the agent into the condensate. In some embodiments, incorporation of the agent into the condensate is detected without using a detectable tag. In some embodiments, incorporation of the agent into the condensate is detected using Raman spectroscopy, spectrophotometry and quantitative phase microscopy, or spin down assay. In some embodiments, the agent comprises a detectable tag. In some embodiments, the detectable tag is a fluorescent tag.

In some embodiments, the method comprises contacting the agent having a detectable tag with the composition comprising the condensate, measuring incorporation of the agent having a detectable tag into the condensate, contacting the composition comprising the condensate and the agent having a detectable tag with a control agent not having a detectable tag, and again measuring incorporation of the agent having a detectable tag into the condensate. In some embodiments, the method comprises contacting a plurality of agents with a plurality of compositions each having condensates comprising the same condensate components.

In some embodiments, the condensate has a detectable tag. In some embodiments, the viral protein or fragment thereof comprises a detectable tag.

In some embodiments, the viral protein is a coronavirus viral protein. In some embodiments, the coronavirus viral protein is a SARS-CoV-2 viral protein. In some embodiments, the SARS-CoV-2 viral protein is non-structural protein 7 (Nsp7, e.g., Accession: YP_009742614.1, YP_009725303.1), non-structural protein 8 (Nsp8, e.g., Accession: YP_009742615.1, YP_009725304.1), non-structural protein 12 (Nsp12, e.g., Accession: YP_009725307.1), or nucleocapsid protein (e.g., Accession: YP_009724397.2). In some embodiments, the viral protein or fragment thereof comprises an intrinsically disordered region (IDR). In some embodiments, the viral protein or fragment thereof is part of a fusion protein.

In some embodiments, the incorporation of the agent is measured relative to a control. In some embodiments, the incorporation of a plurality of agents is measured and compared to each other.

In some embodiments, the agent is an anti-viral agent or an analog or derivative thereof. In some embodiments, the anti-viral agent is RNA dependent RNA polymerase (RdRP) inhibitor, a chain terminator, an anti-sense molecule, or an analog or derivative thereof. In some embodiments, the relative amount of agent incorporated in the condensate, or not incorporated in the condensate, is measured. In some embodiments, the condensate is physically associated with RNA.

In some embodiments, the condensate is in a cell. In some embodiments, the cell is a virally infected cell. In some embodiments, the condensate is in vitro. In some embodiments, the stability or size of the condensate after contact with the agent is measured. In some embodiments, the condensate comprises or is associated with an RNA dependent RNA polymerase having transcriptional activity and wherein the transcriptional activity is measured after contact with the agent.

Some aspects of the present disclosure are directed to a method of modulating the partitioning of an agent into a condensate comprising a viral protein or fragment thereof comprising modifying the agent, thereby modulating the partitioning of the agent into the condensate. In some embodiments, the partitioning of the agent into the condensate is increased. In some embodiments, the therapeutic efficacy of the modified agent is increased as compared to an unmodified agent. In some embodiments, side effects of the modified agent are decreased as compared to unmodified agent. In some embodiments, the modification of the agent comprises modifying the agent to increase or decrease the number of aromatic side chains. In some embodiments, the viral protein is a coronavirus viral protein. In some embodiments, the coronavirus viral protein is a SARS-CoV-2 viral protein. In some embodiments, the SARS-CoV-2 viral protein is non-structural protein 7 (Nsp7), non-structural protein 8 (Nsp8), non-structural protein 12 (Nsp12), or nucleocapsid protein.

Some aspects of the present disclosure are directed to a method of screening for a candidate agent with modulated condensate partitioning comprising modifying an agent with a condensate partition coefficient and measuring the condensate partition coefficient of the modified agent in a condensate comprising a viral protein or fragment thereof, wherein if the modified agent has a different partition coefficient than the agent, then the modified agent is identified as a candidate agent with modulated condensate partitioning. In some embodiments, the condensate partition coefficient of the modified agent is measured in an in vitro condensate. In some embodiments, the condensate partition coefficient of the modified agent is measured in a condensate in a cell. In some embodiments, the agent with a condensate partition coefficient is an anti-viral agent or an analog or derivative thereof. In some embodiments, the anti-viral agent is an RNA dependent RNA polymerase (RdRP) inhibitor, a chain terminator, an anti-sense molecule, or an analog or derivative thereof. In some embodiments, the candidate agent is modified to increase or decrease to number of aromatic side chains. In some embodiments, the viral protein is a coronavirus viral protein. In some embodiments, the coronavirus viral protein is a SARS-CoV-2 viral protein. In some embodiments, the SARS-CoV-2 viral protein is non-structural protein 7 (Nsp7), non-structural protein 8 (Nsp8), non-structural protein 12 (Nsp12), or nucleocapsid protein. In some embodiments, the viral protein or fragment thereof comprises an intrinsically disordered region (IDR). In some embodiments, the condensate comprises a detectable label. In some embodiments, the modified agent comprises a detectable label. In some embodiments, the stability or size of the condensate after contact with the modified agent is measured. In some embodiments, the condensate comprises or is associated with an RNA dependent RNA polymerase having transcriptional activity and wherein the transcriptional activity is measured after contact with the agent.

Some aspects of the present disclosure are directed to a method of screening for a candidate anti-viral agent with an improved condensate partitioning profile comprising modifying an anti-viral agent with a condensate partition coefficient in a mammalian condensate and measuring the condensate partition coefficient of the modified agent in the mammalian condensate, wherein if the modified anti-viral agent has a reduced partition coefficient in the mammalian condensate than the antiviral agent, then the modified agent is identified as a candidate anti-viral agent with an improved condensate partitioning profile.

In some embodiments, the condensate partition coefficient of the modified anti-viral agent is measured in an in vitro condensate. In some embodiments, the condensate partition coefficient of the modified agent is measured in a condensate in a mammalian cell. In some embodiments, the anti-viral agent is an RNA dependent RNA polymerase (RdRP) inhibitor, a chain terminator, an anti-sense molecule, or an analog or derivative thereof. In some embodiments, the candidate anti-viral agent is modified to increase or decrease to number of aromatic side chains. In some embodiments, the mammalian condensate comprises a detectable label. In some embodiments, the modified anti-viral agent comprises a detectable label.

Some aspects of the present disclosure are directed to a composition comprising a cell having a first condensate comprising a first detectable label and a second condensate having a different second detectable label, wherein the first condensate comprises a viral protein or fragment thereof and the second condensate is selected from a transcriptional condensate, super-enhancer condensate, splicing speckle condensate, heterochromatin condensate, or nucleolus. In some embodiments, the composition further comprises an agent contacted with the cell. In some embodiments, the agent is a known anti-viral agent or analog or derivative thereof. In some embodiments, the agent is a candidate anti-viral agent.

Some aspects of the present disclosure are directed to a composition comprising a first in vitro condensate comprising a viral protein or fragment thereof, a second in vitro condensate and an agent contacted with the first and second in vitro condensate. In some embodiments, the second in vitro condensate is a mammalian condensate. In some embodiments, the second in vitro condensate is a transcriptional condensate.

Some aspects of the present disclosure are directed to an in vitro condensate comprising one or more SARS-CoV-2 viral proteins or fragments thereof. In some embodiments, the SARS-CoV-2 viral protein is non-structural protein 7 (Nsp7), non-structural protein 8 (Nsp8), non-structural protein 12 (Nsp12), or nucleocapsid protein. In some embodiments, the SARS-CoV-2 viral protein or fragment thereof comprises an intrinsically disordered region (IDR). In some embodiments, the SARS-CoV-2 viral protein or fragment thereof is part of a fusion protein. In some embodiments, the condensate comprises a detectable label. In some embodiments, the condensate comprises or is associated with a RNA dependent RNA polymerase capable of transcription in the presence of RNA. In some embodiments, the condensate comprises or is associated with RNA.

Some aspects of the present disclosure are directed to a method of characterizing the transcriptional inhibitory activity of an agent, comprising providing a composition having a condensate comprising SARS-CoV-2 Nsp7, SARS-CoV-2 Nsp8, SARS-CoV-2 Nsp12, and SARS-CoV-2 Nucleocapsid, or functional fragments thereof, in contact with an RNA template and nucleotides, contacting the composition with an agent, and measuring transcription of the RNA template. In some embodiments, condensate is an in vitro condensate. In some embodiments, the condensate is in a transgenic cell. In some embodiments, the nucleotides comprise a detectable label. In some embodiments, the method further comprises comparing transcription in the present of the agent to a control composition not contacted with the agent. In some embodiments, the agent is an anti-viral agent or analog or derivative thereof. In some embodiments, the anti-viral agent is a chain terminator. In some embodiments, a plurality of agents are screened.

Some aspects of the present disclosure are directed to a composition having an in vitro condensate comprising SARS-CoV-2 Nsp7, SARS-CoV-2 Nsp8, SARS-CoV-2 Nsp12, and SARS-CoV-2 Nucleocapsid, or functional fragments thereof, in contact with an RNA template and nucleotides. In some embodiments, the composition further comprises an agent in contact with the condensate.

BRIEF DESCRIPTION OF THE DRAWINGS

FIG. 1A is a schematic of the drug partitioning assay. FIG. 1B are fluorescent micrographs (Confocal Microscopy, 100×Objective). Left column-nucleocapsid condensate signal, Middle column-drug signal, Right column-merged signals. FIG. 1C shows the enrichment ratios in nucleocapsid condensates for each drug.

FIG. 3A is a schematic of a condensate comprising Nsp7, Nsp8, Nsp12 (RNA-dependent RNA polymerase), and nucleocapsid. FIG. 3B shows a schematic of viral replication-transcription condensate assay. FIG. 3C are photomicrographs at 150×objective. Rightmost panel shows colocalization of Nsp7, Nsp8, Nsp12 (RNA-dependent RNA polymerase), and nucleocapsid.

FIG. 4A is a schematic of the drug partitioning assay in Nsp8 condensates. FIG. 4B are photomicrographs (confocal microscopy, 100×objective) of labeled Nsp8 in the presence of various drugs. Results show that Mitoxantrone enhances Nsp8 condensate formation and size.

DETAILED DESCRIPTION OF THE INVENTION

Figures 1A, 1B:
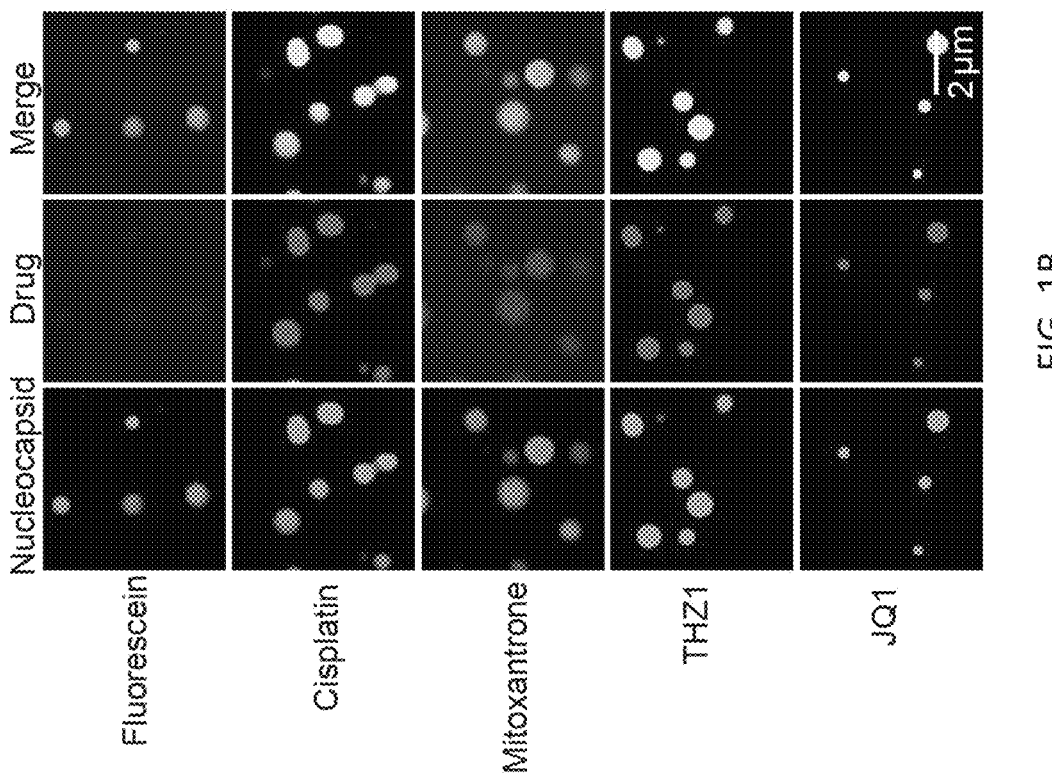
FIGS. 1A-1C show that small molecule drugs are concentrated within nucleocapsid condensates. Streptavidin tagged nucleocapsid was expressed in HEK cells and purified from cell lysates with biotin beads. Purified protein was then chemically labeled with amine-reactive Pac-Blue fluorescent dye. 10 uM of this protein was mixed in droplet formation buffer with 10% PEG and 1-50 uM of each of the fluorescent drugs and imaged under a confocal fluorescent microscope as previously described (Klein et al, Science 2019).
Figure 1C:
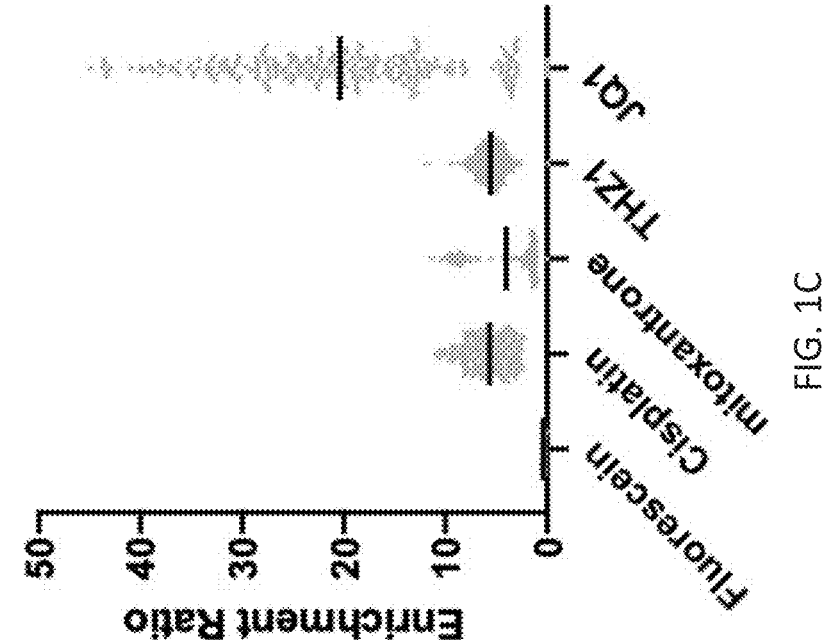
Figure 2:
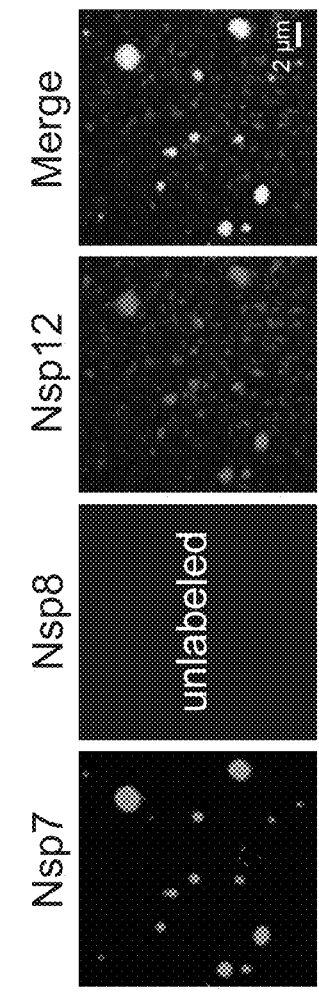
FIG. 2 showsNsp7, Nsp8 and Nsp12 (RNA-dependent RNA polymerase) co-phase separate in vitro. Streptavidin tagged Nsp7, Nsp8, or Nsp12, was expressed in HEK cells and purified from cell lysates with biotin beads. Purified protein was then chemically labeled with amine-reactive Alexa Fluor 488 (for Nsp7) or amine-reactive Alexa Fluor 647 (for Nsp12). These proteins were mixed together as follows: 5 uM Nsp7-488, 5 uM Nsp8, 0.25 uM Nsp12-647, 90 mM KCl, 45 mM HEPES, 3 mM MgCl2, 5% glycerol, 10% PEG, then imaged under a confocal fluorescent microscope as described (Klein et al, Science 2020). Left side of FIG. is a schematic of a droplet containing Nsp7, Nsp8, and Nsp12-reconstituting a viral replication-transcription condensate in vitro. Right side are confocal micrographs at 150× of Nsp7, Nsp8, Nsp12. Rightmost micrograph shows that Nsp7, Nsp8, and Nsp12 form droplets together.
Figure 2:
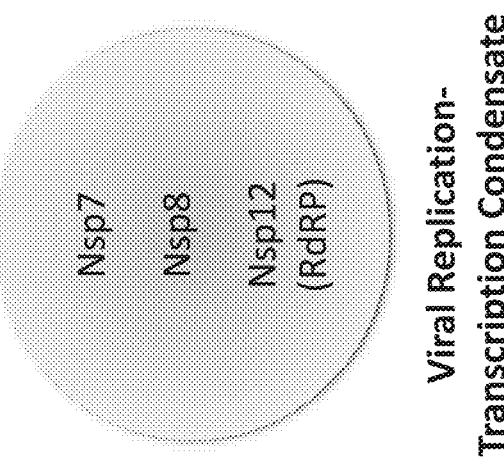

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), Current Protocols in Molecular Biology, Current Protocols in Immunology, Current Protocols in Protein Science, and Current Protocols in Cell Biology, all John Wiley & Sons, N.Y., edition as of December 2008; Sambrook, Russell, and Sambrook, Molecular Cloning: A Laboratory Manual, 3rd ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; 10th ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, MD) and National Center for Biotechnology Information, National Library of Medicine (Bethesda, Md), as of May 1, 2010, ncbi.nlm nih.gov/ omim/ and in Online Mendelian Inheritance in Animals (OMIA), a database of genes, inherited disorders and traits in animal species (other than human and mouse), at omia.angis.org.au/contact.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

The inventors have discovered SARS-CoV-2 proteins (the virus causing COVID-19) in condensates in infected cells. The inventors have further discovered that SARS-CoV-2 proteins can form condensates in vitro and can partition drugs in the absence of the target for the drug. Thus, disclosed herein are methods of screening for agents that can partition in SARS-CoV-2 condensates and therefore may be effective anti-viral agents. Also disclosed are methods of optimizing the activity and/or reducing the side effects of known or suspected anti-viral agents by screening modified known or suspected anti-viral agents for partitioning in viral condensates and other condensates occurring in cells (e.g., transcriptional condensates).

Some aspects of the present disclosure are directed to a method of characterizing an agent, comprising contacting the agent with a composition (e.g., solution) comprising a condensate comprising a viral protein or fragment thereof, and measuring incorporation of the agent in the condensate. In some embodiments, the method further comprises determining if the agent is a possible anti-viral agent based on whether the agent is present at an appropriate concentration in the condensate. In some embodiments, the method further comprises characterizing a plurality of agents (e.g., drug candidates) and selecting one or more lead agents having a desirable or optimal condensate partitioning profile (e.g., concentrating in a viral condensate and/or not concentrating in a non-viral condensate in an infected cell). In some embodiments, the method comprises contacting a plurality of agents with a plurality of compositions each having condensates comprising the same condensate components.

In some embodiments, the method further comprises selecting an agent that has a relatively high partition coefficient as compared with other agents tested (e.g., in top 20%, in the top 10%, in the top 5%) and (ii) testing the selected agent in an assay for its effect on transcriptional activity of a viral condensate, viral translation or replication. In some embodiments, the method further comprises selecting an agent that has a relatively high partition coefficient as compared with other agents tested (e.g., in top 20%, in the top 10%, in the top 5%), conjugating the selected agent to a known anti-viral compound or active fragment thereof (e.g., chain terminator), and testing the selected agent in an assay for its effect on transcriptional activity of a viral condensate, viral translation or replication.

In some further embodiments of the methods disclosed throughout the specification, an agent identified as having a desired property (e.g., its ability to partition into a viral condensate, ability to inhibit formation of viral condensate, ability to disrupt existing viral condensates, increased partitioning into viral as compared to non-viral condensate(s), etc.), is tested in a further assay (e.g., in a cell-free system, in cells, in organoids, in animals (e.g., mice, rats, non-human primates, bats, monkeys) for its potential efficacy as an antiviral agent. In some embodiments, the further assay measures production of viral transcripts by viral transcriptional condensate. In some embodiments, the further assay measures production of viral transcripts by virus-infected cells. In some embodiments, the further assay measures production of viral proteins by virus-infected cells. In some embodiments, the further assay measures production of viral particles. In some embodiments, the further assay measures production of infectious viral particles. In some embodiments, the further assay measures the effect on duration and/or severity of symptoms and/or other manifestations of disease in virus-infected subjects (e g animal subjects). In some embodiments the agent is tested in cell culture, e.g., using virus-infected cells. In some embodiments, the cells are mammalian epithelial cells, e.g., lung epithelial cells, olfactory epithelial cells, enterocytes. In some embodiments the cells are primary cells. In some embodiments the cells are members of a cell line. In some embodiments the agent is tested in organoids, e.g., lung organoids, intestinal organoids. In some embodiments the agent is tested in a virus-infected non-human animal.

Methods of making in vitro condensates with non-viral components, as well as manipulating condensates and determining condensate partitioning coefficients, condensate morphology, condensate morphology can be found in WO 2019/183552 published Sep. 26, 2019, as well as in Hnisz et al., 2017. *Cell* 169, 13-23; Bradner et al., 2017. *Cell* 168, 629-643; Zamudio et al., 2019. *Mol. Cell* 76, 753-766.e6; and Boija et al., 2018. *Cell* 175, 1842-1855.e16, each incorporated by reference in its entirety.

The term "agent" as used herein means any compound or substance such as, but not limited to, a small molecule, nucleic acid, polypeptide, peptide, drug, ion, etc. An "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In some embodiments, the agent is selected from the group consisting of a nucleic acid, a small molecule, a polypeptide, and a peptide.

In some embodiments, the agent is a small molecule. The term "small molecule" refers to an organic molecule that is less than about 2 kilodaltons (kDa) in mass. In some embodiments, the small molecule is less than about 1.5 kDa, or less than about 1 kDa. In some embodiments, the small molecule is less than about 800 Daltons (Da), 600 Da, 500 Da, 400 Da, 300 Da, 200 Da, or 100 Da. Often, a small molecule has a mass of at least 50 Da. In some embodiments, a small molecule is non-polymeric. In some embodiments, a small molecule is not an amino acid. In some embodiments, a small molecule is not a nucleotide. In some embodiments, a small molecule is not a saccharide. In some embodiments, a small molecule contains multiple carbon-carbon bonds and can comprise one or more heteroatoms and/or one or more functional groups important for structural interaction with proteins (e.g., hydrogen bonding), e.g., an amine, carbonyl, hydroxyl, or carboxyl group, and in some embodiments at least two functional groups. Small molecules often comprise one or more cyclic carbon or heterocyclic structures and/or aromatic or polyaromatic structures, optionally substituted with one or more of the above functional groups. In some embodiments, the small molecule comprises at least one, at least two, at least three, at least four, at least five, at least six, at least seven, at least eight, at least nine, at least ten or more aromatic side chains.

In certain embodiments, agents are small molecule having a chemical moiety. For example, chemical moieties included unsubstituted or substituted alkyl, aromatic, or heterocyclyl moieties including macrolides, leptomycins and related natural products or analogues thereof. Compounds can be known to have a desired activity and/or property, or can be selected from a library of diverse compounds. In some embodiments, the agent is sufficiently small to diffuse into a condensate. In some embodiments, the agent is less than about 4.4 kDa. In some embodiments, the agent has a partition coefficient for a condensate comprising a viral protein or fragment thereof of at least 100, 150, 200, 300, 350, 400, 450, 500, 550, 600, 650, 700 or more. In some embodiments, the agent has a partition coefficient for a condensate not comprising a viral protein of less than about 10, 20, 50, 100, 150, 200, 300, 350, 400, 450, 500, 550, or 600.

In some embodiments, the agent is a protein or polypeptide. The term "polypeptide" refers to a polymer of amino acids linked by peptide bonds. A protein is a molecule comprising one or more polypeptides. A peptide is a relatively short polypeptide, typically between about 2 and 100 amino acids (aa) in length, e.g., between 4 and 60 aa; between 8 and 40 aa; between 10 and 30 aa. The terms "protein", "polypeptide", and "peptide" may be used interchangeably. In general, a polypeptide may contain only standard amino acids or may comprise one or more non-standard amino acids (which may be naturally occurring or non-naturally occurring amino acids) and/or amino acid analogs in various embodiments. A "standard amino acid" is any of the 20 L-amino acids that are commonly utilized in the synthesis of proteins by mammals and are encoded by the genetic code. A "non-standard amino acid" is an amino acid that is not commonly utilized in the synthesis of proteins by mammals Non-standard amino acids include naturally occurring amino acids (other than the 20 standard amino acids) and non-naturally occurring amino acids. An amino acid, e.g., one or more of the amino acids in a polypeptide, may be modified, for example, by addition, e.g., covalent linkage, of a moiety such as an alkyl group, an alkanoyl group, a carbohydrate group, a phosphate group, a lipid, a polysaccharide, a halogen, a linker for conjugation, a protecting group, a small molecule (such as a fluorophore), etc. In some embodiments, the agent is a protein or polypeptide comprising at least 5, at least 10, at least 15, at least 20, at least 25, at least 30, or more aromatic amino acids.

In some embodiments, the agent consists of or comprises DNA or RNA or a derivative or analog thereof.

In some embodiments, the agent is a peptide mimetic. The terms "mimetic," "peptide mimetic" and "peptidomimetic" are used interchangeably herein, and generally refer to a peptide, partial peptide or non-peptide molecule that mimics the tertiary binding structure or activity of a selected native peptide or protein functional domain (e.g., binding motif or active site). These peptide mimetics include recombinantly or chemically modified peptides, as well as non-peptide agents such as small molecule drug mimetics.

The agent may be a known drug. The type of drug is not limited any may be any suitable drug. In some embodiments, the agent is a known anti-viral agent or an analog or derivative thereof. In some embodiments, the anti-viral agent is a polymerase inhibitor (e.g., RNA dependent RNA polymerase), a chain terminator (e.g., a nucleoside analog), a helicase inhibitor, a protease inhibitor, or an antisense molecule. In some embodiments, the agent is a derivative or analog of a known antiviral agent. In some embodiments, the derivative of the known anti-viral agent comprises one or more additional chemical moieties (e.g., aromatic side chains) that increases the partitioning coefficient of the agent in a condensate comprising a viral protein or fragment thereof (e.g., a viral condensate in a virally infected cell, a SARS-CoV-2 viral condensate in a SARS-CoV-2 infected cell). In some embodiments, the derivative of the known anti-viral agent has one or more deleted chemical moieties as compared to the known agent that increases the partitioning coefficient of the agent in a condensate comprising a viral protein or fragment thereof (e.g., a viral condensate in a virally infected cell, a SARS-CoV-2 viral condensate in a SARS-CoV-2 infected cell).

In some specific embodiments, the agent is a chain terminator or a derivative or analog thereof. As used herein, the term "chain terminator" refers to a nucleotide analog that serves as a substrate for a nucleic acid polymerase enzyme, but once incorporated onto the end of a growing polynucleotide chain, the analog cannot itself serve as a substrate for the attachment of subsequent nucleotide residues, or, in some cases terminates transcription after the addition of a few more residues (e.g., a delayed chain terminator). Examples of chain terminators include the dideoxynucleoside triphosphates ddA, ddC, ddG, and ddT, although other analogs can also serve as chain terminators (e.g., the phosphonomethoxyethyl nucleotide analogs).

In some embodiments, the agent is an adenosine analog, cytidine analog, thymidine analog, guanosine analog, uridine analog.

In some embodiments, the known antiviral agent is ribavirin, indinavir, saquinavir, lopinavir/ritonavir, acyclovir, or remdesivir. In other embodiments, the known anti-viral agent is Apricitabine, Abacavir, Didanosine, Emtricitabine, Lamivudine, Stavudine, Tenofovir alafenamide, Tenofovir disoproxil fumarate, vidarabine, galidesivir, cytarabine, idoxuridine trifluridine, emtricitabine, lamivudine, zalcitabine, abacavir, entecavir, stavudine, telbivudine, or zidovudine. In other embodiments, the anti-viral agent is triphosphates ddA, ddC, ddG, or ddT, nevirapine, delavirdine, efavirenz, etravirine, rilpivirine, or doravirine.

In some embodiments, the agent is exogenous RNA. In some embodiments, the exogenous RNA is a naturally occurring RNA sequence, a modified RNA sequence (e.g., a RNA sequence comprising one or more modified bases), a synthetic RNA sequence, or a combination thereof. As used herein a "modified RNA" is an RNA comprising one or more modifications (e.g., RNA comprising one or more nonstandard and/or non-naturally occurring bases) to the RNA sequence (e.g., modifications to the backbone and or sugar). Methods of modifying bases of RNA are well known in the art. Examples of such modified bases include those contained in the nucleosides 5-methylcytidine (5mC), pseudouridine (Ψ), 5-methyluridine, 2'0-methyluridine, 2-thiouridine, N-6 methyladenosine, hypoxanthine, dihydrouridine (D), inosine (I), and 7-methylguanosine (m7G). It should be noted that any number of bases in a RNA sequence can be substituted in various embodiments. It should further be understood that combinations of different modifications may be used.

In some aspects, the exogenous RNA sequence is a morpholino. Morpholinos are typically synthetic molecules, of about 25 bases in length and bind to complementary sequences of RNA by standard nucleic acid base-pairing. Morpholinos have standard nucleic acid bases, but those bases are bound to morpholine rings instead of deoxyribose rings and are linked through phosphorodiamidate groups instead of phosphates. Morpholinos do not degrade their target RNA molecules, unlike many antisense structural types (e.g., phosphorothioates, siRNA). Instead, morpholinos act by steric blocking and bind to a target sequence within a RNA and block molecules that might otherwise interact with the RNA. In some embodiments, the synthetic RNA is as described in WO 2017075406. In some embodiments, the exogenous RNA are phosphorodiamidate morpholino oligomers (PMOs). See, e.g., Renaud, et. al., Journal of Virology May 2007, 81 (11) 5637-5648.

In some embodiments an RNA sequence can vary in length from about 8 base pairs (bp) to about 200 bp, about 500 bp, or about 1000 bp. In some embodiments, the RNA sequence can be about 9 to about 190 bp; about 10 to about 150 bp; about 15 to about 120 bp; about 20 to about 100 bp; about 30 to about 90 bp; about 40 to about 80 bp; about 50 to about 70 bp in length.

In some embodiments, the exogenous RNA is modified to increase its partitioning coefficient in a condensate comprising a viral protein (e.g., a SARS-CoV-2 viral condensate). In some embodiments, the exogenous RNA is modified to decrease its partitioning coefficient in a condensate not containing a viral protein (e.g., a non-SARS-CoV-2 viral condensate). In some embodiments, the exogenous RNA decreases transcription of viral genes. In some embodiments, the exogenous RNA decreases viral replication.

In some embodiments, agent is exogenous interference RNA (RNAi). As used herein, the term "RNA interference" ("RNAi") (also referred to in the art as "gene silencing" and/or "target silencing", e.g., "target mRNA silencing") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. In some embodiments, exogenous RNA is stabilized by protecting (capping) one or both ends of the RNA by methods known in the art.

In some embodiments, the agent comprises a protein transduction domain (PTD). A PTD or cell penetrating peptide (CPP) is a peptide or peptoid that can traverse the plasma membrane of many, if not all, mammalian cells. A PTD can enhance uptake of a moiety to which it is attached or in which it is present. Often such peptides are rich in arginine. For example, the PTD of the Tat protein of human immunodeficiency viruses types 1 and 2 (HIV-1 and HIV-2) has been widely studied and used to transport cargoes into mammalian cells. See, e.g., Fonseca S B, et al., Adv Drug Deliv Rev., 61(11):953-64, 2009; Heitz F, et al., Br J Pharmacol., 157(2):195-206, 2009, and references in either of the foregoing, which are incorporated herein by reference. In some embodiments, the cell penetrating peptide is HIV-TAT.

In some embodiments, the agent is capable of binding to a target (e.g., a viral polymerase, viral helicase, a viral protease, a viral capsid protein or precursor thereof, a viral nucleic acid, a viral protein, a non-structural viral protein). In some embodiments, the target is present in the composition comprising the condensate. In some embodiments, the target is predominantly present (e.g., at least 51%, at least 60%, at least 70%, at least 80%, at least 90%, at least 95%, at least 97%, at least 99%, at least 99.5%, at least 99.9%, at least 99.99%, or more) outside of the condensate. In some embodiments, the concentration of the target outside of the condensate is at least 2-fold, at least 3-fold, at least 4-fold, at least 5-fold, at least 6-fold, at least 7-fold, at least 8-fold, at least 9-fold, at least 10-fold, at least 20-fold, at least 50-fold, at least 100-fold, or more than the concentration of the target inside the condensate. In some embodiments, the target is predominantly present (e.g., at least 51%, at least 60%, at least 70%, at least 80%, at least 90%, at least 95%, at least 97%, at least 99%, at least 99.5%, at least 99.9%, at least 99.99%, or more) in the condensate. In some embodiments, the concentration of the target in the condensate is at least 2-fold, at least 3-fold, at least 4-fold, at least 5-fold, at least 6-fold, at least 7-fold, at least 8-fold, at least 9-fold, at least 10-fold, at least 20-fold, at least 50-fold, at least 100-fold, or more than the concentration of the target outside the condensate.

In some embodiments, the agent is a candidate agent as described herein. In some embodiments, the agent is resultant from an agent that has been modified to modulate incorporation into a condensate comprising a viral protein or fragment thereof. In some embodiments, the agent is resultant from the coupling or linking of a first agent and second agent as described herein.

In some embodiments, the agent (e.g., candidate agent, modified agent) consists of or comprises a peptide, polypeptide or protein and the number of aromatic rings is increased by substituting one or more non-aromatic amino acid residues with an aromatic amino acid residue (e.g., phenylalanine, tryptophan, tyrosine, and/or histidine). In some embodiments, the agent (e.g., candidate agent, modified agent) consists of or comprises a peptide, polypeptide or protein and the number of aromatic rings is increased by adding one or more aromatic amino acids. In some embodiments, the aromatic amino acid residue is not histidine. In some embodiments, the aromatic amino acid residue is phenylalanine. In some embodiments, the aromatic amino acid residue is a non-naturally occurring amino acid residue or a nonstandard amino acid residue (e.g., L-DOPA (1-3,4-dihydroxyphenylalanine)).

In some embodiments, the agent (e.g., candidate agent, modified agent) consists of or comprises a peptide, polypeptide or protein and the number of aromatic rings is decreased by replacing one or more aromatic amino acids with non-aromatic amino acids (e.g., alanine). In some embodiments, the number of aromatic rings is decreased by deleting or modifying one or more aromatic amino acids.

In some embodiment, the number of aromatic rings is decreased by deleting, modifying, and/or replacing two or more aromatic amino acids.

In some embodiments, the agent (e.g., candidate agent, modified agent) comprises an IDR. In some embodiments, a modified agent comprises an IDR. Regions of intrinsic disorder, also termed intrinsic (or intrinsically) disordered regions (IDR) or intrinsic (or intrinsically) disordered domains can be found in many protein condensate components. Each of these terms is used interchangeably throughout the disclosure. IDR lack stable secondary and tertiary structure. In some embodiments, an IDR may be identified by the methods disclosed in Ali, M., & Ivarsson, Y. (2018). High-throughput discovery of functional disordered regions. *Molecular Systems Biology*, 14(5), e8377. IDRs are known in the art and any suitable method may be used to identify an IDR.

In some embodiments, the modified agent has increased affinity for a condensate comprising a viral protein or fragment thereof. In some embodiments, the modified agent has increased affinity for a condensate comprising a specific condensate component (e.g., a specific viral protein). In some embodiments, the modified agent has at least 1.5-fold, 2-fold, at least 3-fold, at least 4-fold, at least 5-fold, at least 6-fold, at least 7-fold, at least 8-fold, at least 9-fold, at least 10-fold, at least 20-fold, at least 50-fold, at least 100-fold greater affinity for a condensate than a corresponding unmodified agent.

'In some embodiments, the modified agent has an increased partitioning into a condensate comprising a viral protein or fragment thereof relative to an unmodified agent. In some embodiments, the modified agent has increased partitioning into a condensate comprising a specific condensate component (e.g., a specific viral protein). In some embodiments, the modified agent has at least 1.5-fold, 2-fold, at least 3-fold, at least 4-fold, at least 5-fold, at least 6-fold, at least 7-fold, at least 8-fold, at least 9-fold, at least 10-fold, at least 20-fold, at least 50-fold, at least 100-fold greater partition coefficient with respect to a viral condensate than a corresponding unmodified agent.

In some embodiments, the modified agent has decreased affinity for a condensate not containing a viral protein (e.g., a transcriptional condensate, a heterochromatin condensate, splicing speckle condensate, nucleolus, chromatin condensate, polycomb condensate, DNA damage repair condensate, or a condensate physically associated with mRNA initiation or elongation complexes) as compared to the unmodified agent. These condensates not containing a viral protein (e.g., a transcriptional condensate, a heterochromatin condensate, splicing speckle condensate, nucleolus, chromatin condensate, polycomb condensate, DNA damage repair condensate, or a condensate physically associated with mRNA initiation or elongation complexes) may be condensates in, isolated from, or containing components of mammalian cell condensates (e.g. human, non-human primate, rodent, bat). It is noted that the term "transcriptional condensate" as used herein is to describe condensates not containing viral proteins or fragments thereof and is different than the term "viral transcriptional condensate" as used herein.

In some embodiments, the modified agent has affinity for a second agent. In some embodiment, the modified agent is capable of increasing the concentration or amount of the second agent in a condensate comprising a viral protein or fragment thereof by least 2-fold, at least 3-fold, at least 4-fold, at least 5-fold, at least 6-fold, at least 7-fold, at least 8-fold, at least 9-fold, at least 10-fold, at least 20-fold, at least 50-fold, at least 100-fold, or more as compared to the concentration or amount of the second agent in the condensate not in the presence of the modified agent. In some embodiment, the modified agent is capable of decreasing the concentration or amount of the second agent in a condensate comprising a viral protein or fragment thereof by least 2-fold, at least 3-fold, at least 4-fold, at least 5-fold, at least 6-fold, at least 7-fold, at least 8-fold, at least 9-fold, at least 10-fold, at least 20-fold, at least 50-fold, at least 100-fold, or more as compared to the concentration or amount of the second agent in the condensate not in the presence of the modified agent.

In some embodiments, the agent binds to or interacts with a target. The target is not limited. In some embodiments, the target is a viral protein or viral nucleic acid. In some embodiments, the target is a viral polymerase (e.g., RNA dependent RNA polymerase), viral helicase, viral protease, viral non-structural protein, or viral structural protein or precursor thereof. In some embodiments, the target is a SARS-CoV-2 protein or RNA. In some embodiments, the target is a condensate component (e.g., a SARS-CoV-2 condensate component).

As used herein, the phrase "a condensate component" or the like refers to a peptide, protein, nucleic acid, signaling molecule, lipid, or the like that is part of a condensate or has the capability of being part of a condensate (e.g., a condensate comprising a viral protein or fragment thereof, a condensate comprising a coronavirus protein or fragment thereof, a condensate comprising). In some embodiments, the component is within the condensate. In some embodiments, the component is necessary for condensate formation or stability. In some embodiments, the component is not necessary for condensate formation or stability. In some embodiments, the component is a protein or peptide and comprises one or more intrinsically ordered domains. In some embodiments, the component is a non-structural member of a condensate (e.g., not necessary for condensate integrity). In some embodiments, a condensate comprises, consists of, or consists essentially of 1, 2, 3, 4, 5, 6, 7, 8, 9, 10 or more components (e.g., comprises, consists of, or consists essentially of 1, 2, 3, 4, 5, 6, 7, 8, 9, 10 or more viral proteins and/or fragments thereof; comprises, consists of, or consists essentially of 1, 2, 3, 4, 5, 6, 7, 8, 9, 10 or more SARS-CoV-2 viral proteins or fragments thereof). In some embodiments, the condensate comprises, consists of, or essentially consists of 1, 2, 3, or all of SARS-CoV-2 non-structural protein 7 (Nsp7), SARS-CoV-2 non-structural protein 8 (Nsp8), SARS-CoV-2 non-structural protein 12 (Nsp12), and SARS-CoV-2 nucleocapsid protein. In some embodiments, the condensate comprises or consists of SARS-CoV-2 Nsp8 and SARS-CoV-2 nucleocapsid. In some embodiments, a condensate (e.g., an in vitro condensate) does not comprise a nucleic acid. In some embodiments, a condensate (e.g., an in vitro condensate) does not comprise RNA. In some embodiments, the component is a fragment of a protein or nucleic acid. In some embodiments, the size of the fragment is at least about 40%, 50%, 60%, 70%, 80%, 90%, or 95% of the size (e.g., length) of the full length protein or amino acid. In some embodiments, the fragment is a protein and comprises at least 1, 2, 3, 4, 5, 6 or more IDRs. In some embodiments, the condensate component is a viral protein or fragment thereof, or a fusion protein comprising a viral protein or fragment thereof. In some embodiments, the viral protein is a viral non-structural protein. In some embodiments, the viral protein is a viral polymerase, viral helicase, or viral protease. In some embodiments, the condensate component is a viral nucleic acid (e.g., a coronavirus RNA, e.g., a SARS-CoV-2 RNA. In some embodiments, the viral protein or fragment thereof is a coronavirus protein or fragment thereof. In some embodiments, the viral protein or fragment thereof is a SARS-CoV-2 protein or fragment thereof. In some embodiments, the SARS-CoV-2 viral protein is non-structural protein 7 (Nsp7), non-structural protein 8 (Nsp8), non-structural protein 12 (Nsp12), or nucleocapsid protein. In some embodiments, the condensate component comprises one or more IDRs. In some embodiments, the condensate (e.g., a condensate comprising a SARS-CoV-2 protein or fragment thereof) is transcriptionally active. In some embodiments, the condensate comprises or is physically associated with a polymerase (e.g., a viral polymerase, a coronavirus RNA polymerase, an RNA-dependent RNA polymerase). In some embodiments, the condensate comprises SARS-CoV-2 Nsp7, Nsp8, Nsp12, and Nucleocapsid protein. In some embodiments, the condensate further comprises an RNA template molecule. In some embodiments, the condensate is contacted with nucleotides (e.g., the condensate is transcriptionally active). In some embodiments, the condensate is an in vitro condensate and comprises SARS-CoV-2 Nsp7, Nsp8, Nsp12, and Nucleocapsid protein, comprises or is physically associated with an RNA template, and is in a solution comprising nucleotides and an agent (e.g., a chain terminator or derivative or analog thereof, a modified chain terminator).

In some embodiments, the agent is contacted with a condensate comprising a viral protein or fragment thereof (e.g., SARS-CoV-2 viral protein or fragment thereof) and not comprising or associated with the target (e.g., the target is not present in the composition (solution) comprising the condensate). In some embodiments, the agent is contacted with a condensate comprising a viral protein or fragment thereof (e.g., SARS-CoV-2 viral protein or fragment thereof) and comprising or associated with the target.

As used herein, condensates refer to phase-separated multi-molecular assemblies. In some embodiments, condensates refer to in vitro condensates (sometimes referred to herein as "droplets"). In some embodiments, in vitro condensates are artificially created with one or more condensate components in a solution. In some embodiments, the in vitro condensate comprises components mimicking a condensate found in a virally infected cell (e.g., a SARS-CoV-2 infected cell). In some embodiments, an in vitro condensate is isolated from a virally infected cell (e.g., a SARS-CoV-2 infected cell). In some embodiments, the condensate is physically associated with RNA (e.g., viral RNA transcript, coronavirus RNA transcript, SARS-CoV-2 RNA transcript).

As used herein, "transcriptional condensates" are phase-separated multi-molecular assemblies that occur at the sites of transcription and are high density cooperative assemblies of multiple components that can include transcription factors, co-factors (e.g., co-activator), chromatin regulators, DNA, non-coding RNA, nascent RNA, RNA polymerase II, kinases, proteasomes, topoisomerase, and/or enhancers. As used herein, a "super-enhancer condensate" is a transcriptional condensate occurring at a super-enhancer. Super-enhancers are known in the art. See, e.g., US patent application publication No. 20140287932 A1, incorporated herein by reference. As used herein, "heterochromatin condensates" are phase-separated multi-molecular assemblies that are physically associated with (e.g., occur on) heterochromatin. Heterochromatin condensates have been shown to be associated with repression of gene transcription. As used herein, condensates physically associated with an mRNA initiation or elongation complex are phase-separated multi-molecular assemblies occurring at the relevant complex. In some embodiments, a condensate physically associated with an elongation complex comprises splicing factors. In some embodiments, a condensate physically associated with an elongation complex is a splicing speckle. As used herein, a "splicing speckle" (also sometimes referred to as a nuclear speckle or interchromatin granule cluster) is a condensate enriched in splicing factors. See, e.g., Y. Chen, A. S. Belmont, Genome organization around nuclear speckles. *Curr. Opin. Genet. Dev.* 55, 91-99 (2019), incorporated herein by reference. As used herein, a "nucleolus" or "nucleoli" (plural form) is a condensate comprising RNA and protein occurring in the nucleus. See, e.g., M. Feric et al., Coexisting Liquid Phases Underlie Nucleolar Subcompartments. *Cell.* 165, 1686-1697 (2016), incorporated herein by reference. As used herein, "chromatin condensates" are phase-separated multi-molecular assemblies that are physically associated with chromatin. See, Gibson et al., Organization of Chromatin by Intrinsic and Regulated Phase Separation, Cell (2019), incorporated herein by reference. As used herein, "polycomb condensates" are phase-separated multi-molecular assemblies that physically associate with chromatin and can suppress gene transcription. See, Plys, et al., Phase separation of Polycomb-repressive complex 1 is governed by a charged disordered region of CBX2, Genes Dev. 2019 Jul. 1; 33(13-14):799-813, incorporated herein by reference. As used herein, "DNA damage repair condensates" are phase-separated multi-molecular assemblies that physically associate with double stranded DNA breaks. See, Pessina et al., Functional transcription promoters at DNA double-strand breaks mediate RNA-driven phase separation of damage-response factors, Nature Cell Biology volume 21, pages 1286-1299 (2019), incorporated herein by reference.

Any suitable means of isolation of a condensate from a cell or composition is encompassed herein. In some embodiments, a condensate is chemically or immunologically precipitated. In some embodiments, a condensate is isolated by centrifugation (e.g., at about 5,000×g, 10,000×g, 15,000×g for about 5-15 minutes; about 10.000×g for about 10 min). A condensate may be isolated from a cell by lysis of the nucleus of a cell with a homogenizer (i.e., Dounce homogenizer) under suitable buffer conditions, followed by centrifugation and/or filtration to separate the condensate.

In some embodiments, the condensate is present in a virally infected cell (e.g., SARS-CoV-2 infected cell). The condensate may be a naturally occurring condensate in a virally infected cell. In other embodiments, the condensate may occur in a transgenic cell or an otherwise manipulated cell. In some embodiments, the cell is a mammalian cell (e.g., human or mouse). In some embodiments, the cell expresses angiotensin-converting enzyme 2 on its surface. In some embodiments, the cell expresses Transmembrane protease, serine 2 (TMPRSS2). In some embodiments, the cell is a epithelial cell, a epithelial cell of the lung, a pneumocyte, an enterocyte, or a goblet cell.

In some embodiments, incorporation of the agent into the condensate comprising a viral protein or fragment thereof is detected without using a detectable tag. In some embodiments, incorporation of the agent into the condensate is detected using Raman spectroscopy, spectrophotometry and quantitative phase microscopy, or spin down assay.

In some embodiments, the agent naturally fluoresces. In some embodiments, the agent has a color that differentiates it from condensate and/or from the background or area outside the condensate. In some embodiments, incorporation of the agent is detected by Raman spectroscopy (see, e.g., Smith et al., *Analyst,* 2016, 141, pp. 3590-3600). In some embodiments, incorporation of the agent is detected by nuclear magnetic resonance (NMR). In some embodiments, incorporation of the agent is detected by mass spectrometry. In some embodiments, incorporation of the agent is detected by spectrophotometry and quantitative phase microscopy. In some embodiments, incorporation of the agent is detected by coherence-controlled holographic microscopy. In some embodiments, incorporation of the agent is detected by spin down assay. It will also be appreciated that incorporation of an agent into a condensate may be detected by detecting the amount or proportion of agent that is not incorporated into the condensate.

In some embodiments, incorporation of the agent into the condensate is detected by isolating the condensate from agent not incorporated in the condensate and then measuring agent remaining in the condensate. Any suitable method of isolating a condensate may be used and is not limited. In some embodiments, the condensate is isolated by removal of the condensate from a cell having the condensate. In some embodiments, the condensate is isolated by removal of the condensate from an in vitro composition (e.g., solution) comprising the condensate. In some embodiments, the condensate is crosslinked to assist in isolation of the condensate. In some embodiments, the isolated condensate is disrupted and the amount or proportion of agent measured. Any suitable method of disruption may be used including physical and/or chemical means. In some embodiments, condensates may be disrupted by increasing or decreasing the concentration of salt or crowding agent (e.g., PEG) in the solution. In some embodiments, condensates may be disrupted via sonication, centrifugation, or by varying the temperature. In some embodiments, the agent from the disrupted condensate is measured by chromatography (e.g., HPLC).

In some embodiments, incorporation of the agent in the condensate is measured relative to a control. The control may a compound that is known to incorporate into the condensate under appropriate physiological conditions. The control may also be a compound having similar physical or chemical properties as the agent and having a known incorporation profile into a condensate. In some embodiments, the enrichment ratio or partition coefficient of the agent is determined (i.e., the relative concentrations of the agent in and outside the condensate). In some embodiments, the enrichment ratio is determined by measuring the fluorescence of a fluorescent tag on the agent both in and outside the condensate. In some embodiments, the enrichment ratio is detected by a method described in the Examples section. Methods of determining enrichment ratios and partition coefficients are known in the art and are not limited. In some embodiments, the amount of agent that is partitioned into a condensate is determined.

In some embodiments, the agent comprises a detectable tag (i.e., detectable label). In some embodiments, incorporation of the agent in the condensate is measured using the detectable tag. The term "detectable tag" or "detectable label" as used herein includes, but is not limited to, detectable labels, such as fluorophores, radioisotopes, colorimetric substrates, or enzymes; heterologous epitopes for which specific antibodies are commercially available, e.g., FLAG-tag; heterologous amino acid sequences that are ligands for commercially available binding proteins, e.g., Strep-tag, biotin; fluorescence quenchers typically used in conjunction with a fluorescent tag on the other polypeptide; and complementary bioluminescent or fluorescent polypeptide fragments. A tag that is a detectable label or a complementary bioluminescent or fluorescent polypeptide fragment may be measured directly (e.g., by measuring fluorescence or radioactivity of, or incubating with an appropriate substrate or enzyme to produce a spectrophotometrically detectable color change for the associated polypeptides as compared to the unassociated polypeptides). A tag that is a heterologous epitope or ligand is typically detected with a second component that binds thereto, e.g., an antibody or binding protein, wherein the second component is associated with a detectable label. In some embodiments, the detectable tag is a fluorescent tag. In some embodiments, the detectable tag is amine-reactive Pac-Blue, amine-reactive Alexa Fluor 488, or Alexa Fluor 555.

In some embodiments, a component of the condensate component (e.g., viral protein or fragment thereof, a coronavirus protein or fragment thereof, a SARS-CoV-2 protein or fragment thereof) comprises a detectable tag. In some embodiments, both a condensate component (e.g., viral protein or fragment thereof, a coronavirus protein or fragment thereof, a SARS-CoV-2 protein or fragment thereof) and the agent comprise a detectable tag. In some embodiments, the component comprises a different detectable tag than the agent. In some embodiments, the detectable tag is a tag provided for in the figures and figure legends herein. In some embodiments, the detectable tag is attached to the agent or condensate component (e.g., viral protein or fragment thereof, a coronavirus protein or fragment thereof, a SARS-CoV-2 protein or fragment thereof) via a biotin-streptavidin linkage.

Methods of calculating the incorporation of the agent into a condensate are not limited and may be any method known in the art. In some embodiments, the enrichment ratio of an agent (e.g., an agent having a detectable tag or an agent having a detectable property) for a particular condensate is determined by providing the condensate in solution with the agent and detecting the intensity of the agent in the condensate by confocal microscopy to obtain a $Drug_{in}$ value; providing the condensate in solution without the agent and detecting the intensity of the background within the condensates to obtain a Background value; and providing the agent in solution without the condensate and detecting the intensity of the agent to obtain a $Drug_{diffuse}$ value; wherein the enrichment ratio is equal to $(Drug_{in}-Background)/(Drug_{diffuse})$. In some embodiments, agent partitioning can be determined experimentally by spectrophotometry and quantitative phase microscopy. In some embodiments, a sample composed of two coexisting phases is considered, named dilute and condensed, with volume fractions $\phi$dilute and $\phi$cond=1. If an agent is also present in the sample at an average concentration of ctotal, then mass conservation requires that $$c_{total}=c_{dilute}\phi_{dilute}+c_{cond}\phi_{cond},\qquad(1)$$

where $c_{dilute}$ and $c_{cond}$ are the concentrations of the agent in the dilute and condensed phases, respectively. The partition coefficient is defined for the agent into the condensed phase as $P=c_{cond}/c_{dilute}$. With this definition and the requirement that the phase volume fractions sum to 1, Eq 1 can be written as $$c_{total}=c_{dilute}(1-\phi_{cond})+c_{dilute}P\phi_{cond},\qquad(2)$$

which can be simplified and rearranged to yield $$P = 1 + \left(\frac{c_{total}}{c_{dilute}} - 1\right)(\phi_{cond})^{-1}.\qquad(3)$$

the ratio $c_{total}/c_{dilute}$ is estimated from fluorescence spectroscopy measurements, as described below, while $\phi_{cond}$, it is inferred from the lever rule (M. Rubinstein, R. H. Colby, Polymer Physics (Oxford University Press, 2003)) as follows: denoting the concentration of condensate protein (e.g. viral protein) by s, mass conservation gives stotal=$s_{dilute}\phi_{dilute}+s_{cond}\phi_{cond}$, in analogy with Eq. 1. Again, using the requirement that the volume fractions of coexisting phases sum to 1, this can be rearranged to yield $$\phi_{cond} = \frac{s_{total} - s_{dilute}}{s_{cond} - s_{dilute}},\qquad(4)$$

where $s_{total}$ and $s_{dilute}$ are measured spectrophotometrically from optical absorbance, e.g. at 280 nm, and $s_{cond}$ is measured from quantitative phase microscopy, using e.g., a coherence-controlled holographic microscope.

Uv-vis spectroscopy can be used to estimate the absolute concentration of agent in solution using Beer-Lambert law with Eq 5, $$A=\text{Log } 10(I0/I)=\varepsilon cL\qquad(5)$$

wherein A is the measured absorbance (in Absorbance Units (AU)), I0 is the intensity of the incident light at a given wavelength, I is the transmitted intensity, L the path length through the sample, and c the concentration of the absorbing species. For each species and wavelength, $\varepsilon$ is a constant known as the molar absorptivity or extinction coefficient. This constant is a fundamental molecular property in a given solvent, at a particular temperature and pressure, and has units of 1/M*cm.

In some embodiments, the amount of partitioned agent can be measured by using a spin down assay. Specifically, a known concentration of agent is added with condensate components and droplets are allowed to form. Then the mixture is centrifuged to pellet the droplets, the supernatant collected, and the concentration of agent in the supernatant measured. Amount of agent partitioned can then be determined by subtracting the concentration of agent in the supernatant from the total known concentration of drug added.

In some embodiments, quantitative phase measurements can be performed using a coherence-controlled holographic microscope. Software can be used to construct compensated phase images from acquired holograms. In some embodiments, each phase image is spatially segmented based on intensity, and a window containing each segmented object is fit to a spatial function of the form $$\varphi(x, y) = \frac{2\pi}{\lambda}\Delta n H(x, y \mid R),\qquad(6)$$

where $\varphi(x, y)$ is the phase intensity at pixel location (x, y), $\lambda$ is the illumination wavelength, $\Delta n$ is the refractive index difference between condensates and the surrounding dilute phase, and H(x, y|R) is the projected height of a sphere of radius R. The fitting parameters in Eq. 6 are $\Delta n$ and R. It is assumed that no crowding agent partitions into the condensates and calculate the average scaffold concentration in each filtered condensate as $$s_{cond} = \frac{\Delta n + (n_{dilute} - n_0)}{dn/ds}.\qquad(7)$$

Here $n_0$ is the refractive index of buffer in the absence of scaffold and crowding agent, $n_{dilute}$ is the refractive index of the dilute phase, and both are measured at using digital refractometer. The refractive index increment of the condensate protein, do/ds, can be estimated from amino acid composition.

In some embodiments, agent-target interactions in the presence of a condensate may be modeled. Such modeling may be useful, e.g., for determining an effective partitioning coefficient and/or concentration of an agent to be therapeutically effective against a target (e.g., a viral polymerase, helicase, protease, or nucleic acid). This simplified model was developed of drug-target interactions in the presence of a condensate. The relevant species are the drug (D) (i.e., agent), target (T), and the drug-target complex (D-T). It is assumed that there are only 2-types of phases, the bulk/dilute nuclear phase (n) and the condensate phase (c), which is present with volume fraction $f=V_{condensate}/V_{nucleus}$. At equilibrium, the following partitioning conditions are obeyed:

$$\frac{[D]_c}{[D]_n} = p_D; \frac{[T]_c}{[T]_n} = p_T;$$

where $p_D$, $p_T$ are the partition coefficients of the drug and target. $[D]_c$ represents the concentration of species D in condensate phase (and similarly for other components/phases). In this model, the drug and target complex with phase-independent disassociation constant of $K_D$.

$$[D] + [T] \leftrightarrow^{K_D} [D-T]$$

$$K_D = \frac{[D][T]}{[D-T]}$$

To solve for equilibrium concentrations of various species, which are present at overall levels $[D]_0$, $[T]_0$, the species balance is written down as:

$$f([D]_c+[D-T]_c)+(1-f)([D]_n+[D-T]_n)=[D]_0$$

$$f([T]_c+[D-T]_c)+(1-f)([T]_n+[D-T]_n)=[DT]_0$$

These 6 concentrations are solved with 2-equations and 4 constraints (2 from partitioning and 2 from reaction equilibria). The fraction of bound target is defined as:

$$\text{Fraction}_{bound}, c = \frac{[D-T]_c}{[D]_c + [T]_c}$$

A similar expression is used for the fraction of bound target in the nuclear (bulk or dilute) phase. In case of controls plotted, plot fraction is plotted when there is only 1 phase (f=0).

The presence of a detectable tag on an agent may, in some cases, alter the incorporation activity of the agent into a condensate. However, if the labeled agent incorporated into a condensate that can be flushed out with an excess of unlabeled agent, then the incorporation of the labeled agent into the condensate is not, or partially not, mediated by the label.

Thus, in some embodiments, the methods disclosed herein comprise contacting an agent having a detectable tag with the composition comprising the condensate having a viral protein or fragment thereof, measuring incorporation of the agent having a detectable tag into the condensate, contacting the composition (e.g., solution) comprising the condensate and the agent having a detectable tag with a control agent not having a detectable tag (i.e., an identical agent not having the detectable tag), and again measuring incorporation of the agent having a detectable tag into the condensate. In some embodiments, the condensate comprises or consists of one or more of SARS-CoV-2 viral protein non-structural protein 7 (Nsp7), non-structural protein 8 (Nsp8), non-structural protein 12 (Nsp12), or nucleocapsid protein, or a fragment thereof. In some embodiments, at least an equal concentration of control agent is contacted. In some embodiments, an excess of control agent is contacted (e.g., at least 2-fold, at least 3-fold, at least 4-fold, at least 5-fold, at least 6-fold, at least 7-fold, at least 8-fold, at least 9-fold, at least 10-fold, at least 20-fold, at least 50-fold, at least 100-fold, or more of control agent). In some embodiments, a condensate incorporating a tagged agent is contacted with an increasing gradient of control agent and loss of tagged agent is measured continuously or at discrete intervals.

In some embodiments, a component of the condensate (e.g., a viral protein or fragment thereof, a SARS-CoV-2 protein or fragment thereof) comprises a detectable tag. In some embodiments, both the agent and a component of the condensate comprise a detectable tag. The detectable tag is not limited and may be any detectable tag disclosed herein. In some embodiments, DNA or RNA incorporated into or associated with the condensate comprises a detectable tag.

In some embodiments, provided herein are methods of characterizing an agent comprising providing a fusion construct comprising a condensate component (e.g., viral protein, SARS-CoV-2 protein) or functional fragment thereof and a nucleic acid binding domain contacted with a nucleic acid capable of binding with the nucleic acid binding domain, and contacting the fusion construct with the agent, thereby characterizing the agent. In some embodiments, the fusion construct anchors a condensate comprising the condensate component or functional fragment to the nucleic acid and the agent is contacted with the condensate. In some embodiments, the agent is contacted with the fusion construct along with one or more condensate components capable of forming a condensate with the fusion construct.

In some embodiments, the nucleic acid binding domain is LacI and the nucleic acid comprises lac operator sequences (e.g., a lac array).

In some embodiments, the fusion construct further comprises a detectable tag. The detectable tag is not limited and may be any detectable tag disclosed herein. In some embodiments, the detectable tag is a fluorescent tag. In some embodiments, a component of the condensate other than the fusion construct condensate component or functional fragment comprises a detectable tag. The detectable tag is not limited and may be any detectable tag disclosed herein. In some embodiments, the detectable tag is a fluorescent tag. In some embodiments, both the fusion construct and the component of the condensate other than the fusion construct condensate component or functional fragment thereof each comprise a detectable tag. In some embodiments, the fusion construct and the component of the condensate other than the fusion construct condensate component or functional fragment thereof each comprise a detectable tag and the ability of the agent to modulate the amount of condensate component associated with the fusion construct is measured by detecting co-localization of each detectable tag.

In some embodiments, the fusion construct further comprises a linker between the nucleic acid binding domain and the condensate component or functional fragment. The linker is not limited and may be any linker described herein. In some embodiments, the linker is GAPGSAGSAAGGSG (SEQ ID NO: 1).

In some embodiments of the methods disclosed herein, the stability, morphology, or size of the condensate after contact with the agent is measured. In some embodiments, the condensate comprises or consists of one or more of SARS-CoV-2 viral protein non-structural protein 7 (Nsp7), non-structural protein 8 (Nsp8), non-structural protein 12 (Nsp12), or nucleocapsid protein, or a fragment thereof. In some embodiments, methods disclosed herein (e.g., confocal microscopy, Raman microscopy) are used to measure condensate size or morphology after contact with the agent. In some embodiments, the size or morphology of the condensate after contact with the agent is compared to a control. In some embodiments, the control is an identical condensate or control condensate not contacted with the agent. In some embodiments, the control is the condensate prior to contact with the agent. In some embodiments, the methods disclosed herein comprise determining if the condensate dissolves after contact with an agent. In some embodiments, the methods disclosed herein comprise determining the period of time after contact with the agent until dissolution of the condensate. In some embodiments, the period of time is compared to a control (e.g., a condensate not contacted with the agent). In some embodiments, the stability, morphology, or size of a condensate comprising a viral protein or fragment thereof (e.g., SARS-CoV-2 protein or fragment thereof) is assessed after contact with a plurality of agents (e.g., each agent is contacted with an identical condensate). In some embodiments, the plurality of agents are analogs or derivatives of a base agent. In some embodiments, the effect of the different agents is compared to each other (e.g., to determine optimal modifications to the base agent).

In some embodiments, the ability of an agent to suppress or prevent formation of a condensate comprising a viral protein or fragment thereof is assessed. In some embodiments, the condensate comprises or consists of one or more of SARS-CoV-2 viral protein non-structural protein 7 (Nsp7), non-structural protein 8 (Nsp8), non-structural protein 12 (Nsp12), or nucleocapsid protein, or a fragment thereof. In some embodiments, a solution comprising an agent is contacted with one or more condensate components comprising, consisting, or consisting essentially of viral proteins or fragments thereof under conditions wherein the condensate components form a condensate in the absence of the agent and formation of the condensate is assessed. In some embodiments, assessing formation of the condensate comprises determining if the condensate forms and/or how long it takes the condensate to form. In some embodiments, the amount of time it takes to form the condensate is compared to a control (e.g., the time it takes to form the condensate in the absence of the agent).

In some embodiments, the ability of the agent to modulate the number of condensates comprising a viral protein or fragment thereof is assessed. In some embodiments, the condensate comprises or consists of one or more of SARS-CoV-2 viral protein non-structural protein 7 (Nsp7), non-structural protein 8 (Nsp8), non-structural protein 12 (Nsp12), or nucleocapsid protein, or a fragment thereof. In some embodiments, the ability of the agent to modulate the number of condensates measures the ability of the agent to modulate condensate stability. In some embodiments, a solution comprising the agent is contacted with one or more condensate components comprising, consisting, or consisting essentially of viral proteins or fragments thereof under conditions wherein the condensate components form a condensate in the absence of the agent and the number of condensates formed is compared to a control (e.g., a solution comprising the condensate components and not the agent). In some embodiments, a solution is contacted with the agent and one or more condensate components comprising, consisting, or consisting essentially of viral proteins or fragments thereof simultaneously under conditions wherein the condensate components form a condensate in the absence of the agent and the number of condensates formed is compared to a control (e.g., a solution comprising the condensate components and not the agent). In some embodiments, a solution comprising one or more condensate components comprising, consisting, or consisting essentially of viral proteins or fragments thereof is contacted with the agent under conditions wherein the condensate components form a condensate in the absence of the agent and the number of condensates formed is compared to a control (e.g., a solution comprising the condensate components and not the agent).

In some embodiments of the methods disclosed herein, the condensate comprises or is associated with an RNA dependent RNA polymerase having transcriptional activity and wherein the transcriptional activity is measured after contact with the agent. In some embodiments, transcriptional activity is compared to a control (e.g., transcriptional activity of a control condensate not contacted with the agent). In some embodiments, viral transcript activity (e.g., rate) is determined (e.g., compared to a control). In some embodiments, the condensate comprises of one or more of SARS-CoV-2 viral protein non-structural protein 7 (Nsp7), non-structural protein 8 (Nsp8), non-structural protein 12 (Nsp12), or nucleocapsid protein, or a fragment thereof.

Some aspects of the disclosure provide a method of characterizing an agents ability to inhibit transcription comprising providing a condensate comprising, consisting, or consisting essentially of SARS-CoV-2 Nsp7, SARS-CoV-2 Nsp8, SARS-CoV-2 Nsp12, and SARS-CoV-2 Nucleocapsid, or functional fragments thereof, in contact with an RNA template and nucleotides, contacting the condensate with an agent and measuring transcription (e.g., as compared to a control (e.g., a control condensate not contacted with the agent)). In some embodiments, the condensate is an in vitro condensate. In some embodiments, the condensate is in a cell (e.g., human cell). In some embodiments, the cell is a transgenic cell modified to express of SARS-CoV-2 Nsp7, SARS-CoV-2 Nsp8, SARS-CoV-2 Nsp12, and SARS-CoV-2 Nucleocapsid. In some embodiments, the nucleotides comprise a detectable label (e.g., a radioactive label). In some embodiments, the method is part of a high throughput screen wherein multiple agents (e.g., multiple modified agents) are contacted with condensates, for example in a multi-well plate. In some embodiments, the agents are known or suspected antiviral agents or analogs or derivatives thereof. In some embodiments, the agents are chain terminators or analogs or derivatives thereof. In some embodiments, the agents are obtained from a library of agents. In some embodiments, the library comprises agents which have modifications of known or suspected anti-viral agents.

In some embodiments of the methods disclosed herein, viral replication is measured after contact of the condensate comprising a viral protein with the agent as compared to a control. In some embodiments, the control is a condensate not contacted with the agent. In some embodiments, the condensate is in a virally infected cell (e.g., a corona virus infected cell, a SARS-CoV-2 infected cell) or a genetically modified cell). In some embodiments, the condensate comprises or consists of one or more of SARS-CoV-2 viral protein non-structural protein 7 (Nsp7), non-structural protein 8 (Nsp8), non-structural protein 12 (Nsp12), or nucleocapsid protein, or a fragment thereof.

Some aspects of the present disclosure are directed to a method of screening for a candidate agent with modulated condensate partitioning comprising modifying an agent with a condensate partition coefficient in a condensate comprising a viral protein or fragment thereof (e.g., coronavirus viral protein or fragment thereof, a SARS-CoV-2 viral protein or fragment thereof) and measuring the condensate partition coefficient of the modified agent, wherein if the modified agent has a different partition coefficient than the agent, then the modified agent is identified as a candidate agent with modulated condensate partitioning. In some embodiments, the candidate agent with modulated condensate partitioning has a higher condensate partitioning ratio than the unmodified agent. In some embodiments, the condensate comprises or consists of one or more of SARS-CoV-2 viral protein non-structural protein 7 (Nsp7), non-structural protein 8 (Nsp8), non-structural protein 12 (Nsp12), or nucleocapsid protein, or a fragment thereof. Modifications may be by well-known medicinal chemistry manipulations and modifications. In some embodiments, the modification increases or decreases the solubility of the agent. In some embodiments, the modification modulates an electrostatic property of the agent. In some embodiments, the modification comprises addition of 1, 2, 3, 4, 5, 6, 7, 8, 9, 10, 15, 20, 25 or more aromatic rings or side chains. In some embodiments, the modification comprises deletion of 1, 2, 3, 4, 5, 6, 7, 8, 9, 10, 15, 20, 25 or more aromatic rings or side chains. In some embodiments, the modification is the coupling of a moiety or second agent that preferentially partitions in a desired condensate comprising a viral protein or fragment thereof. In some embodiments, the modification is the coupling of a moiety or second agent that preferentially does not partition in a one or more condensate types (e.g., a non-viral protein containing condensate, a transcriptional condensate). In some embodiments, the agent to be modified is a known or candidate anti-viral agent. In some embodiments, the agent is a known anti-viral agent or an analog or derivative thereof. In some embodiments, the known or candidate anti-viral agent is a polymerase inhibitor (e.g., RNA dependent RNA polymerase), a chain terminator, a helicase inhibitor, a protease inhibitor, or an antisense molecule. In some embodiments, the known anti-viral agent is an anti-viral agent disclosed herein. In some embodiments, the modified agent is obtained from a library of agents (e.g., a library comprising compounds with modifications of known or candidate therapeutic agents or anti-viral agents) and the partitioning coefficient of the modified agent from the library is assessed.

In some embodiments, the condensate partition coefficient of the modified agent is measured in an in vitro condensate comprising a viral protein or fragment thereof (e.g., coronavirus viral protein or fragment thereof, a SARS-CoV-2 viral protein or fragment thereof). In some embodiments, the in vitro condensate comprises or consists of one or more of SARS-CoV-2 viral protein non-structural protein 7 (Nsp7), non-structural protein 8 (Nsp8), non-structural protein 12 (Nsp12), or nucleocapsid protein, or a fragment thereof. In some embodiments, the condensate partition coefficient of the modified agent is measured in a condensate comprising a viral protein or fragment thereof (e.g., coronavirus viral protein or fragment thereof, a SARS-CoV-2 viral protein or fragment thereof) in a virally infected cell or a genetically modified cell.

In some embodiments, the candidate agent is identified as an improved candidate agent if the candidate agent has increased partitioning into a condensate having a viral protein or fragment thereof (e.g., coronavirus viral protein or fragment thereof, a SARS-CoV-2 viral protein or fragment thereof) and having a target (e.g., viral polymerase, viral helicase, viral protease, viral protein, viral nucleic acid, SARS-CoV-2 polymerase, SARS-CoV-2 helicase, SARS-CoV-2 protease, SARS-CoV-2 protein, SARS-CoV-2 nucleic acid) for the candidate agent. In some embodiments, the condensate comprises or consists of one or more of SARS-CoV-2 viral protein non-structural protein 7 (Nsp7), non-structural protein 8 (Nsp8), non-structural protein 12 (Nsp12), or nucleocapsid protein, or a fragment thereof. In some embodiments, the candidate agent is identified as an improved candidate agent if partitioning is increased by about at least 2-fold, at least 3-fold, at least 4-fold, at least 5-fold, at least 6-fold, at least 7-fold, at least 8-fold, at least 9-fold, at least 10-fold, at least 20-fold, at least 50-fold, at least 100-fold as compared to the unmodified agent. In some embodiments, the candidate agent is identified as an improved candidate agent if partitioning is increased by about 5%, 10%, 15%, 20%, 25%, 30%, 35%, 40%, 45%, 50%, 55%, 60%, 65%, 70%, 75%, 80%, 85%, 90%, 95%, 99% or more as compared to the unmodified agent. In some embodiments, a candidate agent identified as having an improved partitioning coefficient in a condensate comprising a viral protein or fragment thereof is conjugated to an anti-viral compound (e.g., chain terminator). In some embodiments, the conjugate is tested in an assay for its effect on transcriptional activity of a viral condensate, viral translation or replication.

In some embodiments, the candidate agent is identified as an improved candidate agent if the candidate agent has decreased partitioning into a condensate not having a target (e.g., therapeutic target) (e.g., viral polymerase, viral helicase, viral protease, viral protein, viral nucleic acid, SARS-CoV-2 polymerase, SARS-CoV-2 helicase, SARS-CoV-2 protease, SARS-CoV-2 protein, SARS-CoV-2 nucleic acid) for the candidate agent. In some embodiments, the candidate agent is identified as an improved candidate agent if partitioning is decreased by about at least 2-fold, at least 3-fold, at least 4-fold, at least 5-fold, at least 6-fold, at least 7-fold, at least 8-fold, at least 9-fold, at least 10-fold, at least 20-fold, at least 50-fold, at least 100-fold as compared to the unmodified agent. In some embodiments, the candidate agent is identified as an improved candidate agent if partitioning is decreased by about 5%, 10%, 15%, 20%, 25%, 30%, 35%, 40%, 45%, 50%, 55%, 60%, 65%, 70%, 75%, 80%, 85%, 90%, 95%, 99% or more as compared to the unmodified agent.

In some embodiments, the candidate agent is identified as an improved candidate agent if the amount of candidate agent (e.g., total number of molecules of candidate agent, concentration of candidate agent) is modulated (e.g., increased) in a condensate comprising a viral protein or fragment thereof (e.g., coronavirus viral protein or fragment thereof, a SARS-CoV-2 viral protein or fragment thereof) (i.e., candidate of interest) as compared to the unmodified agent. In some embodiments, the condensate comprises or consists of one or more of SARS-CoV-2 viral protein non-structural protein 7 (Nsp7), non-structural protein 8 (Nsp8), non-structural protein 12 (Nsp12), or nucleocapsid protein, or a fragment thereof. In some embodiments, the amount of candidate agent is increased in the condensate of interest. In some embodiments, this increase corresponds to an increase of the partition coefficient into the condensate of interest. However, this increase may also be due to increasing the availability of the candidate agent for incorporation into the condensate. For example, the candidate agent may have reduced partitioning in a condensate that is not of interest making it available for incorporation into the condensate of interest. In some embodiments, the amount of candidate agent is decreased in the condensate of interest.

In some embodiments, modulating the partitioning of a first agent into a condensate (e.g., by modifying the first agent, e.g., coupling the first agent to a second agent-thereby creating a candidate agent) results in an increased concentration of the modified or coupled first agent in the condensate relative to the concentration at which the unmodified/uncoupled first agent would be present in the condensate. In some embodiments, modifying or coupling the first agent increases the partition coefficient of the first agent into the condensate. In some embodiments, modifying or coupling the first agent causes the first agent to have reduced partitioning into a different condensate (e.g., a condensate not containing a viral protein or fragment thereof) in which it would otherwise become concentrated. In some embodiments, modifying or coupling the first agent decreases the partition coefficient of the first agent into the condensate. In some embodiments, modifying or coupling the first agent causes the first agent to have increased partitioning into a different condensate (e.g., condensate not containing a viral protein or fragment thereof) in which it would otherwise become concentrated.

In some embodiments of the methods disclosed herein further comprise characterizing the condensate incorporation (e.g., enrichment ratio) of a plurality of agents (e.g., possible drug candidates, possible drug candidates from families having distinct structural features) for, e.g., lead optimization, in vivo toxicology or efficacy studies, or Phase I clinical studies. In some embodiments, a step of profiling drug candidates against a condensate comprising a viral protein or fragment thereof or a panel of condensates and (1) selecting a candidate that is not undesirably sequestered in condensate(s) that are not a site where the target is expected to be present or active, or (2) selecting a candidate that is concentrated or at least not excluded from condensate(s) that are a site where the target is expected to be present or active, is included. If one is optimizing a lead compound and has a number of different optimized candidates to choose from, this method can help avoid selecting a candidate that has a higher propensity than other candidates to become concentrated in condensates that do not contain the target (or to select a candidate that has a higher propensity than other candidates to become concentrated in condensates that do contain the target).

Some aspects of the present disclosure are directed to a method of screening for a candidate anti-viral agent with an improved condensate partitioning profile comprising modifying an anti-viral agent with a condensate partition coefficient in a mammalian condensate and measuring the condensate partition coefficient of the modified agent in the mammalian condensate, wherein if the modified anti-viral agent has a reduced partition coefficient in the mammalian condensate than the antiviral agent, then the modified agent is identified as a candidate anti-viral agent with an improved condensate partitioning profile. In some embodiments, the condensate partition coefficient of the modified anti-viral agent is measured in an in vitro condensate. In some embodiments, the condensate partition coefficient of the modified agent is measured in a condensate in a mammalian cell. In some embodiments, the anti-viral agent is an RNA dependent RNA polymerase (RdRP) inhibitor, a chain terminator, an anti-sense molecule, or an analog or derivative thereof. In some embodiments, the candidate anti-viral agent is modified to increase or decrease to number of aromatic side chains. In some embodiments, the mammalian condensate comprises a detectable label. In some embodiments, the modified anti-viral agent comprises a detectable label.

Some aspects of the disclosure are directed to a composition comprising an in vitro condensate comprising one or more SARS-CoV-2 viral proteins or fragments thereof. In some embodiments, the SARS-CoV-2 viral protein is non-structural protein 7 (Nsp7), non-structural protein 8 (Nsp8), non-structural protein 12 (Nsp12), or nucleocapsid protein. In some embodiments, the in vitro condensate comprises, consists of, or essentially consists of 1, 2, 3, or all of SARS-CoV-2 non-structural protein 7 (Nsp7), SARS-CoV-2 non-structural protein 8 (Nsp8), SARS-CoV-2 non-structural protein 12 (Nsp12), and SARS-CoV-2 nucleocapsid protein, and/or a functional fragment thereof. In some embodiments, the SARS-CoV-2 viral protein or fragment thereof of the in vitro condensate comprises an intrinsically disordered region (IDR). In some embodiments, the SARS-CoV-2 viral protein or fragment thereof of the in vitro condensate is part of a fusion protein. In some embodiments, the in vitro condensate comprises a detectable label. In some embodiments, the in vitro condensate comprises or is associated with an RNA dependent RNA polymerase capable of transcription in the presence of RNA. In some embodiments, the in vitro condensate comprises or is associated with RNA (e.g., viral RNA transcript, SARS-CoV-2 viral RNA transcript).

Some aspects of the disclosure are directed to a composition comprising a cell having a first condensate comprising a viral protein or fragment thereof (e.g., a coronavirus protein or fragment thereof, a SARS-CoV-2 protein or fragment thereof) and comprising a first detectable label (i.e., detectable tag) and a second condensate having a different second detectable label. In some embodiments, the second condensate is selected from a super-enhancer condensate, splicing speckle condensate, heterochromatin condensate, nucleolus, chromatin condensate, polycomb condensate, or DNA damage repair condensate. In some embodiments, the first and/or second condensate are mammalian condensates (e.g., murine or human) In some embodiments, the first condensate comprises or consists of one or more of SARS-CoV-2 viral protein non-structural protein 7 (Nsp7), non-structural protein 8 (Nsp8), non-structural protein 12 (Nsp12), or nucleocapsid protein, or a fragment thereof. In some embodiments, the second condensate is a transcriptional condensate. In some embodiments, the condensate comprising a viral protein or fragment thereof further comprises or is associated with viral RNA. In some embodiments, the condensate comprising a viral protein or fragment thereof is transcriptionally active. In some embodiments, the cell is replicating virus. In some embodiments, the composition further comprises an agent contacted with the cell. In some embodiments, the agent is a known therapeutic agent. In some embodiments, the agent is a candidate therapeutic agent. The agent is not limited and can be any agent described herein.

Some embodiments are directed towards an article comprising a first in vitro condensate contacted with an agent, a second in vitro condensate contacted with the same agent, and a multi-well plate separating the first and second in vitro condensates into separate wells. In some embodiments, the article further comprises at least a third in vitro condensate contacted with the agent. In some embodiments, the article further comprises at least a fourth in vitro condensate contacted with the agent. The first in vitro condensate comprises a viral protein (e.g., SARS-CoV-2 viral protein) or fragment thereof. The second, third and fourth in vitro condensates can each comprise a component of a different condensate (e.g., a transcriptional condensate, a super-enhancer condensate, splicing speckle condensate, heterochromatin condensate, nucleolus, chromatin condensate, polycomb condensate, or DNA damage repair condensate). In some embodiments, the second, third and fourth in vitro condensates are mammalian condensates (e.g., murine or human). The first, second, third and fourth in vitro condensates can each comprise a different detectable label.

Some embodiments are directed towards an article comprising an in vitro condensate comprising a viral protein or fragment thereof (e.g., a coronavirus protein or fragment thereof, a SARS-CoV-2 protein or fragment thereof) contacted with an agent, the same in vitro condensate contacted with a second agent, and a multi-well plate separating the in vitro condensates into separate wells. In some embodiments, the article further comprises at least an in vitro condensate contacted with a third agent. In some embodiments, the article further comprises at least an in vitro condensate contacted with a fourth agent.

Some embodiments are directed towards an article comprising an in vitro condensate comprising a viral protein or fragment thereof (e.g., a coronavirus protein or fragment thereof, a SARS-CoV-2 protein or fragment thereof) contacted with an agent, the same in vitro condensate contacted with a second agent, and a multi-well plate separating the in vitro condensates into separate wells. In some embodiments, the article further comprises at least an in vitro condensate contacted with a third agent. In some embodiments, the article further comprises at least an in vitro condensate contacted with a fourth agent.

In some embodiments, the agents disclosed herein are contacted with a condensate comprising a viral protein or fragment thereof (e.g., a coronavirus protein or fragment thereof, a SARS-CoV-2 protein or fragment thereof) at an overall concentration of between about 1 nM and 500 μM. For example, the agent can be added to a solution comprising a condensate to provide an overall concentration in the solution of between about 1 nM and 500 μM. In some embodiments, the agent is contacted with a condensate at an overall concentration of between 10 nM and 100 nM, between 10 nM and 1 μM, between 1 μM and 10 μM, between 10 μM and 100 μM, or between 100 μM and 500 μM. In some embodiments, the agent is added to a composition (e.g., solution) comprising condensates to provide an overall concentration of between about 1 nM and 500 μM. In some embodiments, the agent is added to a composition comprising condensates to provide an overall concentration of between 10 nM and 100 nM, between 10 nM and 1 μM, between 1 μM and 10 μM, between 10 μM and 100 μM, or between 100 μM and 500 μM.

In some embodiments, the condensate is in a cell. The type of cell is not limited and may be any cell described herein. In some embodiments the cell is a mammalian cell, e.g., a human or mouse cell. In some embodiments the cell is a somatic cell. In some embodiments the cell is an epithelial cell, e.g., a lung epithelial cell, olfactory epithelial cell, enterocytes. In some embodiments, the cell is a cell genetically modified to produce a viral protein or fragment thereof (e.g., coronavirus viral protein or fragment thereof, a SARS-CoV-2 viral protein or fragment thereof). In some embodiments, the cell is a virally infected cell (e.g., a corona virus infected cell, a SARS-CoV-2 infected cell).

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or prior publication, or for any other reason. All statements as to the date or representation as to the contents of these documents is based on the information available to the applicants and does not constitute any admission as to the correctness of the dates or contents of these documents.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more active agents, additives, ingredients, optional agents, types of organism, disorders, subjects, or combinations thereof, can be excluded.

Where the claims or description relate to a composition of matter, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately".

"Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

EXAMPLES

Implications of Viral Infection on Host Cell Condensates.

The human cell nucleus contains various condensates containing components that govern similar cellular processes. These include the transcriptional condensate marked by MED1 and the heterochromatin condensate marked by HP1a that regulate key aspects of transcriptional regulation, gene activation and gene repression, respectively. To visualize these condensates in non-infected and SARS-CoV-2 infected human epithelial lung cancer cells, immunofluorescence was performed using MED1 and HP1 antibodies. In agreement with what one would expect from dynamic condensates, condensates of varying size and number were found in both conditions.

It was next sought to determine whether SARS-CoV-2 protein also formed condensates in the cell. In this regard, protein disorder is known to promote phase separation and formation of biomolecular condensates. To that end, a Predictor of Naturally Disordered Regions (PONDR) disorder analysis was performed and it was found that Nsp8 (a RdRP cofactor) and Nucleocapsid (a protein binding to the RNA genome) have the highest disorder score of proteins encoded by the SARS-CoV-2 genome. When visualized in SARS-CoV-2 infected human epithelial lung cancer cells using immunofluorescence, Nsp8 and Nucleocapsid were found to condense, increasing the number of condensates found in the cell. Purified recombinant fluorescently labeled versions of Nsp8 and Nucleocapsid were generated and it was found that the two proteins were able to form droplets in an in vitro assay.

Viral Transcription Occurs within Condensates.

Figures 3A, 3B, 3C:
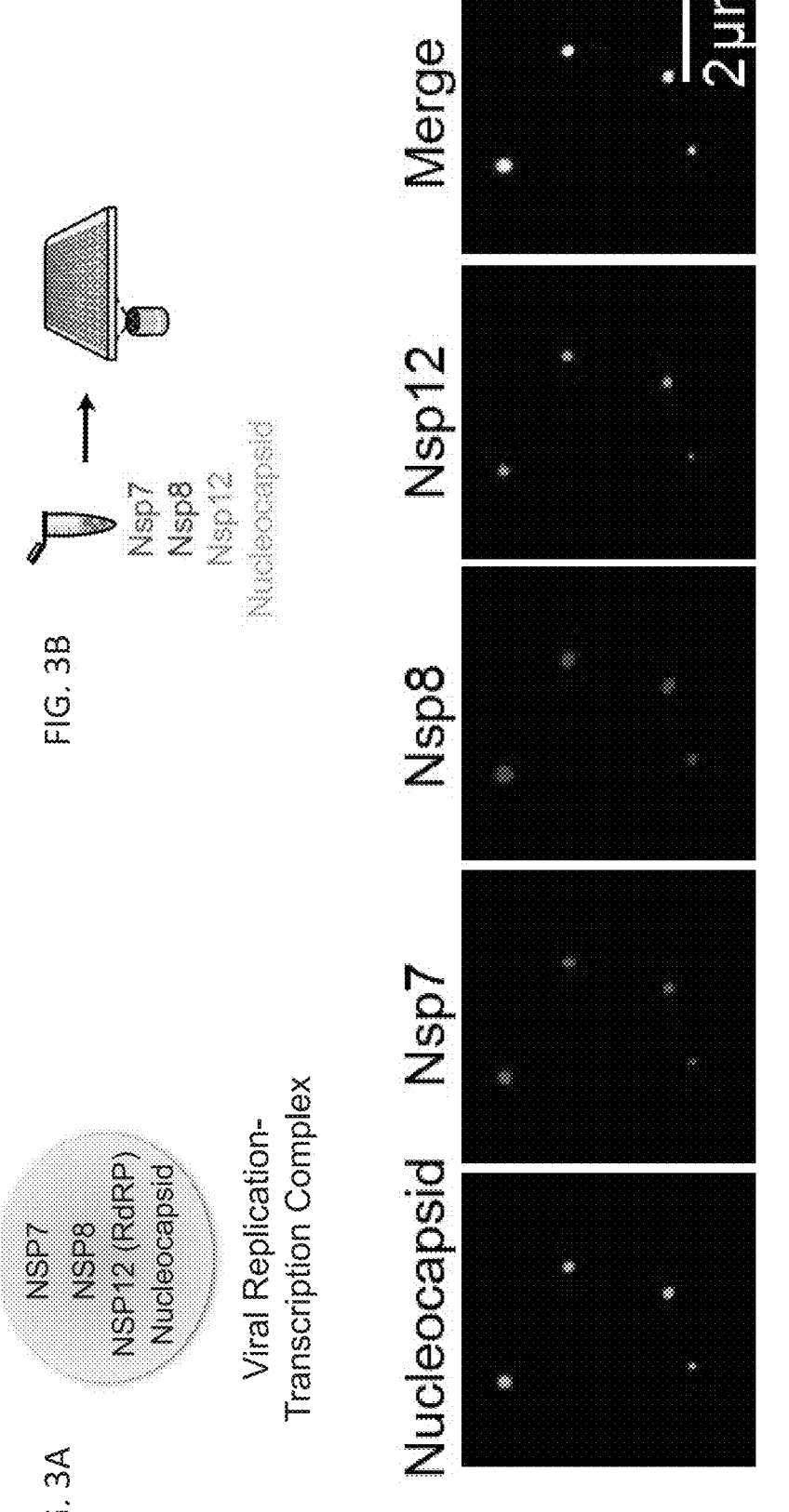
FIGS. 3A-3C show reconstituting a viral replication-transcription condensate with nucleocapsid in vitro. Streptavidin tagged nucleocapsid, Nsp7, Nsp8, or Nsp12, was expressed in HEK cells and purified from cell lysates with biotin beads. Purified protein was then chemically labeled with amine-reactive Alexa Fluor 488 (for Nsp12) or amine-reactive Alexa Fluor 647 (for Nucleocapsid), Pac-Blue (for Nsp8), or Alexa Fluor 555 (for Nsp7). These proteins were mixed together as follows: 2 uM Nucleocapsid-647, 1 uM Nsp7-555, 1 uM Nsp8-405, 50 nM Nsp12 488, 125 mM KCl, 10% PEG then imaged under a confocal fluorescent microscope as described (Klein et al, Science 2020).
Figures 4A, 4B:
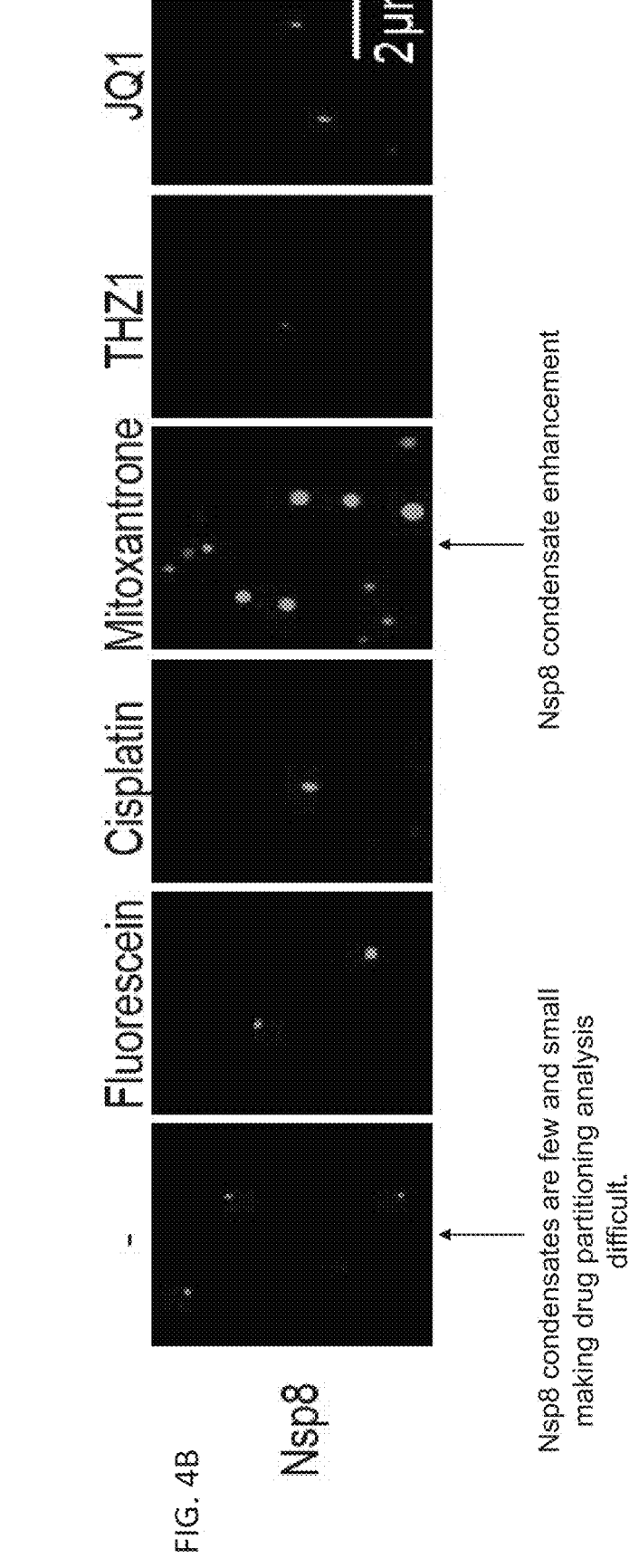
FIGS. 4A-4B show drug mediated enhancement of Nsp8 condensate formation. Streptavidin tagged Nsp8, was expressed in HEK cells and purified from cell lysates with biotin beads. Purified protein was then chemically labeled with amine-reactive Pac-Blue fluorescent dye. 10 uM of this protein was mixed in droplet formation buffer with 10% PEG and 1-50 uM of each drug (50 uM for mitoxantrone) and imaged under a confocal fluorescent microscope as described (Klein et al, Science 2020).

It was hypothesized that key components of the viral transcriptional replication complex and the highly disorder nucleocapsid protein might condense together to drive transcription. To that end purified recombinant Nsp7, Nsp8, Nsp12, and Nucleocapsid, labeled with four distinct fluorescent labels, were produced. When adding the four proteins into a single droplet reaction, it was found that they all condensed together in droplets (FIG. 3C). It was next sought to determine if the in vitro reconstituted viral-transcription condensates are able to perform transcription under these conditions. An in vitro RdRP assay using purified Nsp7, Nsp8, Nsp12, and Nucleocapsid protein, an RNA template and radioactive nucleotides was developed. It was found that the transcriptional machinery within the reconstituted condensates were able to perform transcription. Nucleosides have proven to be useful antiviral drugs, these results indicate that the RdRP assay might be an important screening tool to identify effective antiviral medicine.

Viral Condensates Concentrate Small Molecule with Distinct Chemical Features

Figure 5:
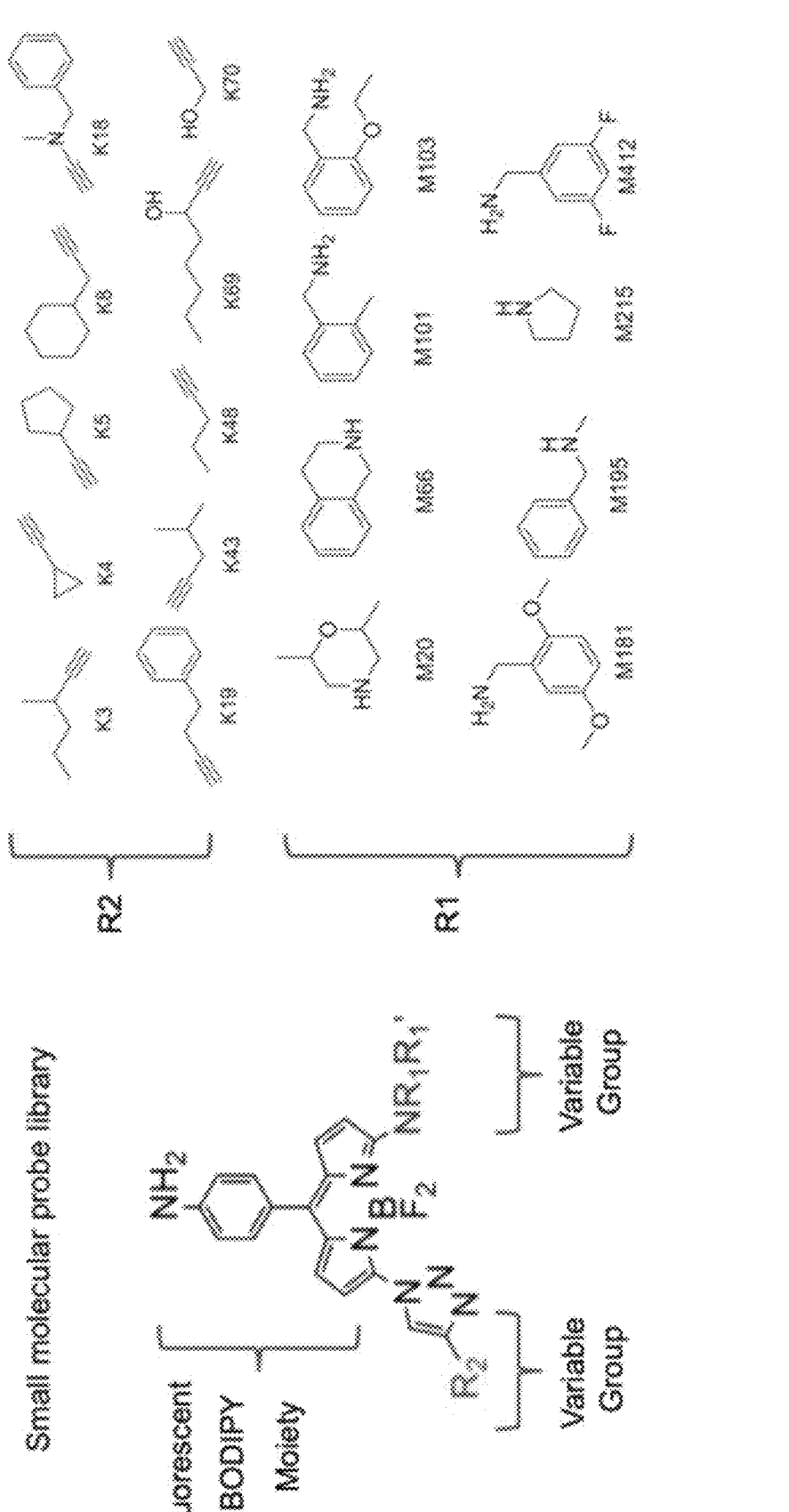
FIG. 5 shows an example of members of a small molecule probe library in which boron-dipyrromethene (BODIPY) is modified with various combinations of chemical side groups.

It was reasoned that the viral transcriptional condensate might provide a means to concentrate antinucleoside drugs (i.e., chain terminators) that are known to be required at high concentration to avoid immediate replacement by the viral proofreading enzyme. To gain additional insight to the chemical features of molecules that mediate partitioning of anti-viral drugs into the viral transcriptional condensate, a small molecule probe library in which boron-dipyrromethene (BODIPY) is modified with various combinations of chemical side groups was screened. The library is composed of 100 compounds in which a fluorescent moiety was modified with various chemical groups, including all major functional groups and the functional groups. An example small molecule probe library in which boron-dipyrromethene (BODIPY) is modified with various combinations of chemical side groups is shown in FIG. 5. The relative ability of the various molecules to concentrate within the viral transcriptional condensate was measured by adding the small molecule to the Nucleocapsid condensate using fluorescence confocal microscopy.

What is claimed is:

1. A method of characterizing an agent, comprising contacting the agent with a composition comprising a condensate comprising SARS-CoV-2 non-structural protein 7 (Nsp7) and SARS-CoV-2 non-structural protein 8 (Nsp8), or functional fragments thereof, and measuring incorporation of the agent into the condensate.

2. The method of claim 1, wherein the agent comprises a detectable tag.

3. The method of claim 1, wherein the SARS-CoV-2 Nsp7, the SARS-CoV-2 Nsp8 or functional fragments thereof comprise a detectable tag.

4. The method of claim 1, wherein the condensate further comprises SARS-CoV-2 nucleocapsid.

5. The method of claim 4, wherein the agent is an anti-viral agent or analog or derivative thereof.

6. The method of claim 1, wherein the incorporation of a plurality of agents is measured and compared to each other.

7. The method of claim 1, wherein the condensate is physically associated with RNA.

8. The method of claim 1, wherein the stability or size of the condensate after contact with the agent is measured.

9. The method of claim 1, wherein the condensate comprises or is associated with an RNA dependent RNA polymerase having transcriptional activity and wherein the transcriptional activity is measured after contact with the agent.

10. An in vitro condensate comprising SARS-CoV-2 non-structural protein 7 (Nsp7) and SARS-CoV-2 non-structural protein 8 (Nsp8), or functional fragments thereof and a detectable label.

11. The condensate of claim 10, wherein the condensate further comprises SARS-CoV-2 non-structural protein 12 (Nsp12) or nucleocapsid protein.

12. The condensate of claim 10, wherein the condensate comprises a SARS-CoV-2 viral protein or fragment thereof that is part of a fusion protein.

13. The condensate of claim 10, wherein the detectable label is a fluorescent label.

14. The condensate of claim 10, wherein the condensate comprises or is associated with a RNA dependent RNA polymerase capable of transcription in the presence of RNA.

15. The condensate of claim 10, wherein the condensate comprises or is associated with RNA.

16. A method of characterizing the transcriptional inhibitory activity of an agent, comprising providing a composition having a condensate comprising SARS-CoV-2 Nsp7, SARS-CoV-2 Nsp8, SARS-CoV-2 Nsp12, and SARS-CoV-2 Nucleocapsid, or functional fragments thereof, in contact with an RNA template and nucleotides, contacting the composition with an agent, and measuring transcription of the RNA template.

17. The method of claim 16, wherein the condensate is an in vitro condensate.

18. The method of claim 16, wherein the nucleotides comprise a detectable label.

19. The method of claim 16, further comprising comparing transcription in the presence of the agent to a control composition not contacted with the agent.

20. The method of claim 16, wherein the agent is an anti-viral agent or analog or derivative thereof.

* * * * *